(12) United States Patent
DeSimone et al.

(10) Patent No.: US 9,205,601 B2
(45) Date of Patent: *Dec. 8, 2015

(54) CONTINUOUS LIQUID INTERPHASE PRINTING

(71) Applicant: Carbon3D, Inc., Redwood City, CA (US)

(72) Inventors: Joseph M. DeSimone, Los Gatos, CA (US); Alexander Ermoshkin, Chapel Hill, NC (US); Nikita Ermoshkin, Chapel Hill, NC (US); Edward T. Samulski, Chapel Hill, NC (US)

(73) Assignee: Carbon3D, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/569,202

(22) Filed: Dec. 12, 2014

(65) Prior Publication Data

US 2015/0097315 A1    Apr. 9, 2015

Related U.S. Application Data

(63) Continuation of application No. PCT/US2014/015506, filed on Feb. 10, 2014.

(60) Provisional application No. 61/919,903, filed on Dec. 23, 2013, provisional application No. 61/865,841, filed on Aug. 14, 2013, provisional application No. 61/763,746, filed on Feb. 12, 2013.

(51) Int. Cl.
*B29C 33/58* (2006.01)
*B29C 33/62* (2006.01)
(Continued)

(52) U.S. Cl.
CPC ......... *B29C 67/0092* (2013.01); *B29C 67/0066* (2013.01); *B29C 67/0088* (2013.01);
(Continued)

(58) Field of Classification Search
CPC   B29C 2033/0005; B29C 33/56; B29C 33/58; B29C 33/62; B29C 35/08; B29C 41/02; B29C 67/0051; B29C 67/0062; B29C 67/0066; B29C 67/007; B29C 67/0085; B29C 67/0092
USPC ................................ 264/40.1, 338, 401, 497
See application file for complete search history.

(56) References Cited

U.S. PATENT DOCUMENTS

| | | |
|---|---|---|
| 4,575,330 A | 3/1986 | Hull |
| 4,801,477 A | 1/1989 | Fudim |

(Continued)

FOREIGN PATENT DOCUMENTS

| | | |
|---|---|---|
| CN | 103029301 A | 4/2013 |
| CN | 203254661 U | 10/2013 |

(Continued)

OTHER PUBLICATIONS

Atala et al. "Engineering Complex Tissues", *Science Translational Medicine*, Nov. 14, 2012, vol. 4, Issue 160, 11 Pages.

(Continued)

*Primary Examiner* — Leo B Tentoni
(74) *Attorney, Agent, or Firm* — Myers Bigel Sibley & Sajovec, P.A.

(57) ABSTRACT

A method of forming a three-dimensional object, comprises providing a carrier and an optically transparent member having a build surface, the carrier and the build surface defining a build region therebetween; filling the build region with a polymerizable liquid; irradiating the build region through the optically transparent member to form a solid polymer from the polymerizable liquid while concurrently advancing the carrier away from the build surface to form the three-dimensional object from the solid polymer, while also concurrently: (i) continuously maintaining a dead zone of polymerizable liquid in contact with the build surface, and (ii) continuously maintaining a gradient of polymerization zone between the dead zone and the solid polymer and in contact with each thereof, the gradient of polymerization zone comprising the polymerizable liquid in partially cured form. Apparatus for carrying out the method is also described.

26 Claims, 15 Drawing Sheets

(51) Int. Cl.
| | |
|---|---|
| *B29C 67/00* | (2006.01) |
| *G03F 7/00* | (2006.01) |
| *B29C 33/00* | (2006.01) |
| *B33Y 10/00* | (2015.01) |
| *B33Y 30/00* | (2015.01) |
| *B33Y 50/02* | (2015.01) |
| *B29K 71/00* | (2006.01) |
| *B29K 105/00* | (2006.01) |

(52) U.S. Cl.
CPC ....... *G03F 7/0037* (2013.01); *B29C 2033/0005* (2013.01); *B29K 2071/02* (2013.01); *B29K 2105/0005* (2013.01); *B29K 2105/0058* (2013.01); *B29K 2827/12* (2013.01); *B29K 2883/005* (2013.01); *B29K 2995/0026* (2013.01); *B29K 2995/0065* (2013.01); *B33Y 10/00* (2014.12); *B33Y 30/00* (2014.12); *B33Y 50/02* (2014.12)

(56) References Cited

U.S. PATENT DOCUMENTS

| | | | |
|---|---|---|---|
| 4,961,154 | A | 10/1990 | Pomerantz et al. |
| 5,059,359 | A | 10/1991 | Hull et al. |
| 5,122,441 | A † | 6/1992 | Lawton |
| 5,143,663 | A | 9/1992 | Leyden et al. |
| 5,143,817 | A | 9/1992 | Lawton et al. |
| 5,171,490 | A | 12/1992 | Fudim |
| 5,192,559 | A | 3/1993 | Hull et al. |
| 5,198,159 | A | 3/1993 | Nakamura et al. |
| 5,236,637 | A | 8/1993 | Hull |
| 5,247,180 | A | 9/1993 | Mitcham et al. |
| 5,263,130 | A | 11/1993 | Pomerantz et al. |
| 5,271,882 | A | 12/1993 | Shirahata et al. |
| 5,391,072 | A † | 2/1995 | Lawton |
| 5,447,822 | A | 9/1995 | Hull et al. |
| 5,523,193 | A | 6/1996 | Nelson |
| 5,529,473 | A | 6/1996 | Lawton et al. |
| 5,554,336 | A | 9/1996 | Hull |
| 5,569,431 | A | 10/1996 | Hull |
| 5,597,520 | A | 1/1997 | Smalley et al. |
| 5,609,812 | A | 3/1997 | Childers et al. |
| 5,609,813 | A | 3/1997 | Allison et al. |
| 5,630,981 | A | 5/1997 | Hull |
| 5,651,934 | A | 7/1997 | Almquist et al. |
| 5,762,856 | A | 6/1998 | Hull |
| 5,772,947 | A | 6/1998 | Hull et al. |
| 5,779,967 | A | 7/1998 | Hull |
| 5,785,918 | A | 7/1998 | Hull |
| 5,814,265 | A | 9/1998 | Hull |
| 5,824,252 | A | 10/1998 | Miyajima |
| 5,945,058 | A | 8/1999 | Manners et al. |
| 6,027,682 | A | 2/2000 | Almquist et al. |
| 6,391,245 | B1 | 5/2002 | Smith |
| 6,500,378 | B1 | 12/2002 | Smith |
| 6,547,552 | B1 | 4/2003 | Fudim |
| 6,563,207 | B2 | 5/2003 | Shinma |
| 6,652,799 | B2 | 11/2003 | Seng et al. |
| 6,942,830 | B2 | 9/2005 | Mulhaupt et al. |
| 7,023,432 | B2 | 4/2006 | Fletcher et al. |
| 7,052,263 | B2 | 5/2006 | John |
| 7,195,472 | B2 | 3/2007 | John |
| 7,318,718 | B2 | 1/2008 | Ueno |
| 7,438,846 | B2 | 10/2008 | John |
| 7,556,490 | B2 | 7/2009 | Wicker et al. |
| 7,573,561 | B2 | 8/2009 | Fries |
| 7,636,610 | B2 | 12/2009 | Schillen et al. |
| 7,709,544 | B2 † | 5/2010 | Doyle |
| 7,783,371 | B2 | 8/2010 | John et al. |
| 7,790,093 | B2 | 9/2010 | Shkolnik et al. |
| 7,831,328 | B2 | 11/2010 | Schillen et al. |
| 7,845,930 | B2 † | 12/2010 | Shkolnik |
| 7,892,474 | B2 † | 2/2011 | Shkolnik |
| 7,894,921 | B2 | 2/2011 | John et al. |
| 7,962,238 | B2 | 6/2011 | Shkolnik et al. |
| 8,003,040 | B2 | 8/2011 | El-Siblani |
| 8,110,135 | B2 | 2/2012 | El-Siblani et al. |
| 8,126,580 | B2 | 2/2012 | El-Siblani et al. |
| 8,286,236 | B2 | 10/2012 | Jung et al. |
| RE43,955 | E | 2/2013 | Shkolnik et al. |
| 8,372,330 | B2 | 2/2013 | El-Siblani et al. |
| 8,394,313 | B2 | 3/2013 | El-Siblani et al. |
| 8,465,689 | B2 | 6/2013 | Sperry et al. |
| 8,658,076 | B2 | 2/2014 | El-Siblani |
| 9,034,568 | B2 | 5/2015 | McLeod |
| 2003/0173713 | A1 | 9/2003 | Huang |
| 2004/0084520 | A1 | 5/2004 | Muehl et al. |
| 2006/0066006 | A1 | 3/2006 | Haraldsson et al. |
| 2007/0063389 | A1 | 3/2007 | John |
| 2007/0260349 | A1 | 11/2007 | John et al. |
| 2008/0038396 | A1 | 2/2008 | John et al. |
| 2008/0063867 | A1 | 3/2008 | Schlienger et al. |
| 2008/0113293 | A1 | 5/2008 | Shkolnik et al. |
| 2008/0174050 | A1 | 7/2008 | Kikuchi |
| 2009/0020901 | A1 | 1/2009 | Schillen et al. |
| 2009/0130449 | A1 | 5/2009 | El-Siblani |
| 2009/0132081 | A1 | 5/2009 | Schillen et al. |
| 2009/0146344 | A1 | 6/2009 | El-Siblani |
| 2010/0249979 | A1 | 9/2010 | John et al. |
| 2010/0323301 | A1 | 12/2010 | Tang |
| 2011/0009992 | A1 | 1/2011 | Shkolnik et al. |
| 2011/0062633 | A1 | 3/2011 | Shkolnik et al. |
| 2011/0089610 | A1 | 4/2011 | El-Siblani et al. |
| 2011/0101570 | A1 | 5/2011 | John et al. |
| 2011/0196529 | A1 | 8/2011 | Shkolnik et al. |
| 2011/0260365 | A1 | 10/2011 | El-Siblani |
| 2013/0292862 | A1 | 11/2013 | Joyce |
| 2013/0295212 | A1 | 11/2013 | Chen et al. |
| 2013/0304233 | A1 | 11/2013 | Dean et al. |
| 2014/0085620 | A1 | 3/2014 | Lobovsky et al. |
| 2014/0265034 | A1 † | 9/2014 | Dudley |

FOREIGN PATENT DOCUMENTS

| | | |
|---|---|---|
| CN | 103895231 A | 7/2014 |
| DE | 41 25 534 A1 | 2/1993 |
| DE | 93 19 405 | 3/1994 |
| DE | 93 19 405.6 | 3/1994 |
| DE | 20 2013 103 446 U1 | 8/2013 |
| IL | 274727 | 10/2011 |
| JP | H08-192469 | 7/1996 |
| WO | 01/72501 A1 † | 10/2001 |
| WO | 0172501 † | 10/2001 |
| WO | WO 01/72501 A1 | 10/2001 |
| WO | WO 2005/110722 A1 | 11/2005 |
| WO | WO 2008/055533 A1 | 5/2008 |
| WO | WO 2009/003696 A2 | 1/2009 |
| WO | WO 2009/003696 A3 | 1/2009 |
| WO | WO 2009/053099 A1 | 4/2009 |
| WO | WO 2009/053100 A1 | 4/2009 |
| WO | WO 2009/053100 A8 | 4/2009 |
| WO | WO 2010/077097 A2 | 7/2010 |
| WO | 2011086450 A2 † | 7/2011 |
| WO | WO 2011/086450 | 7/2011 |
| WO | WO 2011/111957 A2 | 9/2011 |
| WO | WO 2012/024675 A2 | 2/2012 |
| WO | WO 2012/024675 A3 | 2/2012 |
| WO | WO 2012/024675 A9 | 2/2012 |
| WO | WO 2014/165265 A1 | 10/2014 |

OTHER PUBLICATIONS

Bauer et al. "25$^{th}$ Anniversary Article: A Soft Future: From Robots and Sensor Skin to Energy Harvesters", *Adv. Mater.*, 2014, 26, 149-162.

Bauer et al. "High-strength cellular ceramic composites with 3D microarchitecture", *PNAS*, Feb. 18, 2014, vol. 111, No. 7, 2453-2458.

Bertsch, A. et al. "Rapid prototyping of small size objects", *Rapid Prototyping Journal*, 2000, vol. 6, No. 4, pp. 259-266.

Burns, M. "Automated Fabrication-Improving Productivity in Manufacturing", 1993 (ISBN 0-13-119462-3) pp. 40-49.

(56) References Cited

OTHER PUBLICATIONS

Chakraborty et al. "Coarse-grained foldable, physical model of the polypeptide chain", *PNAS*, Aug. 13, 2013, vol. 110, No. 33, 13368-13373.

Chen Y. et al. "A layerless additive manufacturing process based on CNC accumulation", *Rapid Prototyping Journal*, 2011, vol. 17, No. 3, pp. 218-227.

Chi Zhou, "Development of a Multi-material Mask-Image-Projection-based Stereolithography for the Fabrication of Digital Materials", Paper, presented at Solid Freeform Fabrication Symposium 2011, held Aug. 8-10, 2011, 16 pages, University of Southern California, Los Angeles, USA, available at URL http://utwired.engr.utexas.edu/lff/symposium/proceedingsArchive/pubs/Manuscripts/2011/2011-06-Zhou.pdf.

Chisholm et al. "3D printed flow plates for the electrolysis of water: an economic and adaptable approach to device manufacture", *Energy Environ. Sci*, 2014, 7, 3026-3032.

Choi J. et al. "Multiple-material stereolithography", *Journal of Materials Processing Technology*, 2011, vol. 211, Issue 3, pp. 318-328.

Choi J.W. et al. "Multi-material microstereolithography", *Int. J. Adv. Manuf. Technol.*, 2010, vol. 49, pp. 543-551.

Cvetkovic et al. "Three-dimensionally printed biological machines powered by skeletal muscle" *PNAS*, Jul. 15, 2014, vol. 111, No. 28, 10125-10130.

Derby B. "Printing and Prototyping of Tissues and Scaffolds", *Science*, vol. 338, Nov. 16, 2012, 921-926.

Duoss et al. "Three-Dimensional Printing of Elastomeric, Cellular Architectures with Negative Stiffness", *Adv. Funct. Mater.*, 2014, 24, 4905-4913.

Envisiontec, Ultra: The Benchmark in 3-Dimensional Desktop Printing, Technical Data Sheet [no date] from envisiontec.com.

Erkal et al. "3D printed microfluidic devices with integrated versatile and reusable electrodes", *Lab Chip*, 2014, 14, 2023-2032.

Gibson et al. *Additive Manufacturing Technologies: Rapid Prototyping to Direct Digital Manufacturing*, Spring, New York 2010, 472 Pages.

Gonzalez-Meijome et al. "Determination of Oxygen Permeability in Soft Contact Lenses Using a Polarographic Method: Estimation of relevant Physiological Parameters", *Ind. Eng. Chem. Res.*, 2008, 47, 3619-3629.

Gross et al. "Evaluation of 3D Printing and Its Potential Impact on Biotechnology and the Chemical Sciences", *Anal. Chem.*, 2014, 86, 3240-3253.

Han L. et al. "Fabrication of three-dimensional scaffolds for heterogeneous tissue engineering", *Biomed Microdevices*, 2010, No. 12, pp. 721-725.

Han L. et al. "Projection Microfabrication of three-dimensional scaffolds for tissue engineering", *Journal of Manufacturing Science and Engineering*, 2008, vol. 130, 021005.

Huang Y.M. et al. "On-line force monitoring of platform ascending rapid prototyping system", *Journal of Materials Processing Technology*, 2005, vol. 159, pp. 257-264.

Imamdar A. et al. "Development of an automated multiple material stereolithography machine", *Proceedings of Annual Solid Freeform Fabrication Symposium*, 2006, Austin, TX, pp. 624-635.

Kim H. et al. "Scheduling and process planning for multiple material stereolithography", *Rapid Prototyping J.*, 2010, vol. 16, No. 4, pp. 232-240.

Kim H. et al. "Slice overlap detection algorithm for the process planning in multiple material stereolithography", *Int. J. Adv. Manuf. Technol.*, 2010, vol. 46, No. 9, pp. 1161-1170.

Kitson et al. "Bringing Crystal Structures to Reality by Three-Dimensional Printing", *Crystal Growth & Design*, 2014, 14, 2720-2724.

Lipson H. et al. Fabricated: The New World of 3D Printing, 2013 John Wiley & Sons, Indianapolis, Indiana, Chapters 2 & 5, 50 pages.

Lu et al. "A digital micro-mirror device-based system for the microfabrication of complex, spatially patterned tissue engineering scaffolds", *J Biomed Mater Res*, 77A:396-405, 2006.

Maruo S. et al. "Multi-polymer microstereolithography for hybrid opto-MEMS", *Proceedings of the 14$^{th}$ IEEE International Conference on Micro Electro Mechanical Systems (MEMS 2001)*, 2001, pp. 151-154.

Merkel et al. "Gas and Vapor Transport Properties of Perfluoropolymers", Chapter 9, *Materials Science of Membranes for Gas and Vapor Separation*, John Wiley & Sons, Ltd, 2006, 251-270.

Pearce J. "Building Research Equipment with Free, Open-Source Hardware", *Science*, vol. 337, Sep. 14, 2012, 1303-1304.

Rogers et al. "Materials and Mechanicals for Stretchable Electronics", *Science*, vol. 327, Mar. 26, 2010, 1603-1607.

Schaedler et al. "Ultralight Metallic Microlattices", *Science*, vol. 334, Nov. 18, 2011, 962-965.

Suh et al. "Using Stop-Flow Lithography to Produce Opaque Microparticles: Synthesis and Modeling", *Langmuir*, 2011, 27, 13813-13819.

Sun C.N. et al. "Projection micro-stereolithography using digital micro-mirror dynamic mask", *Sensors and Actuators A.*, 2005, vol. 121, pp. 113-120.

Sun et al. "3D Printing of Interdigitated Li-Ion Microbattery Architectures", *Adv. Mater.*, 2013, 25, 4539-4543.

Symes et al. "Integrated 3D-printed reactionware for chemical synthesis and analysis", *Nature Chemistry*, vol. 4, May 2012, 349-354.

Travitzky et al. "Additive Manufacturing of Ceramic-Based Materials", *Advanced Engineering Materials*, vol. 16, No. 6, 2014, 729-754.

Wicker R. et al. "Multiple material micro-fabrication: extending stereo lithography to tissue engineering and other novel applications", *Proceedings of Annual Solid Freeform fabrication Symposium*, 2005, Austin, TX, pp. 754-764.

Yagci et al. "Photoinitiated Polymerization: Advances, Challenges, and Opportunities", *Macromolecules*, 2010, 43, 6245-6260.

Zheng et al. "Ultralight, Ultrastiff Mechanical Metamaterials", *Science*, vol. 344, Issue 6190, Jun. 20, 2014, 1373-1377.

Adzima, Brian, The Ember Printer: An Open Platform for Software, Hardware, and Materials Development, Adzima_UV.ebWest2015, printed from the Internet on Mar. 16, 2015 at URL https://www.slideshare.net/slideshow/embed_code/45733940.

Bylinsky, Gene "Industry's Amazing New Instant Prototypes", Reporter Associate Alicia Hills Moore, Jan. 12, 1998, 12 Pages.

Hornbeck, Larry J. "Digital Light Processing™ for High-Brightness, High-Resolution Applications", Texas Instruments, Feb. 1997, 16 Pages.

Hornbeck, Larry J. From cathode rays to digital micromirrors: A history of electronic projection display technology, Jul.-Sep. 1998, pp. 7-46.

How It Works—Internet Articles, Texas Instruments, Inc., 1997, 15 Pages.

International Search Report and Written Opinion Corresponding to International Application No. PCT/US2014/065874; Date of Mailing: Feb. 19, 2015; 14 Pages.

Kudo3D First Print Checklist and PSP Handling Instructions, Version 1.0, 2015.

Kudo3D Titan 1—Printing Guide, Revision 1.4, 2015.

Kudo3D Titan 1, (Ruby & Diamond Editions), Build Manual, Revision 2.0, 2015.

Wohlers, Terry "Eight years of rapid prototyping", RP Direct, 1997 Directory, 9 Pages.

Tumbleston et al. "Continuous liquid interface production of 3D objects", *Science*, Mar. 16, 2015, 347, 1349, Accepted Feb. 3, 2015.

Tumbleston et al. Supplementary Materials for Continuous liquid interface production of 3D objects, *Science*, Mar. 16, 2015, 347, 1349.

DelViscio, Jeff, "Incredible New 3D Printing Technique Looks Like Sci-Fi", *Popular Mechanics*, Mar. 16, 2015, Retrieved from the internet at URL http://www.popularmechanics.com/technology/a14586/carbon3d-3d-printer-resin/.

Feltman, Rachel, "This mind-blowing new 3-D printing technique is inspired by 'Terminator 2'", *The Washington Post*, Mar. 16, 2015, Retrieved from the internet at URL http://www.washingtonpost.com/news/speaking-of-science/wp/2015/03/16/this-new-technology-blows-3d-printing-out-of-the-water-literally/.

(56) References Cited

OTHER PUBLICATIONS

Shi J et al. Spatially controlled oxygen inhibition of acrylate photopolymerization as a new lithography method for high-performance organic thin-film transistors. Chemistry of Materials. 2010; 22(7): 2341-2346.

Pan Y et al. A fast mask projection stereolithography process for fabricating digital models in minutes. Journal of Manufacturing Science and Engineering. Oct. 2012; 134: 9 pp.

Hribar KC et al. Light-assisted direct-write of 3D functional biomaterials. Lab Chip. Jan. 2014; 14(2): 268-275.

Ligon SC et al. Strategies to reduce oxygen inhibition in photoinduced polymerization. Chemical Reviews. 2014; 114: 557-589.

Anderson C. "Dreaming in 3D", *Wired*, Oct. 2012, p. 136-143 (2012).

Bedal B. et al. "Advances in Part Accuracy", *Stereolithography and Other RP&M Technologies, from Rapid Prototyping to Rapid Tooling*, Paul F. Jacobs, Ph.D., Society of Manufacturing Engineers, p. 149-181, (1996).

Deutsch S. "Plastics for 3D Printing", *Make: Ultimate Guide to 3D Printing 2014*, p. 36-37 (2014).

Dougherty D. "A Brief History of Personal 3D Printing", *Make: Ultimate Guide to 3D Printing 2014*, p. 8 (2014).

Greenemeier L. "To Print the Impossible, Will 3-D printing transform conventional manufacturing?", *Scientific American*, May 2013, vol. 308, No. 5, p. 44-47.

Hausmann R. "How to Make the Next Big Thing", *Scientific American*, May 2013, vol. 308, No. 5, p. 35-36.

Jacbos, P. "Postprocessing", *Rapid Prototyping & Manufacturing, Fundamentals of StereoLithography*, First Edition, Paul F. Jacobs, Ph.D., Society of Manufacturing Engineers, p. 221-248. (1992).

Jacobs, P. "Fundamental Process", *Rapid Prototyping & Manufacturing, Fundamentals of StereoLithography*, First Edition, Paul F. Jacobs, Ph.D., Society of Manufacturing Engineers, p. 79-110. (1992).

Kaziunas France A. "3D Printing Buyer's Guide; Here's how we tested, compared, and rated 30 new 3D printers, scanners, and filament bots", *Make: Ultimate Guide to 3D Printing 2014*, p. 56-95 (2014).

Lockman C. "Meet Your Maker, a New Approach to Product Development", *Perspectives, College of Business at the University of Illinois at Urbana-Champaign*, p. 2-5, Spring 2013.

Mohammadi G. "Jiving with Jarvis; what would you do with a professional 3D printer", *Make: Ultimate Guide to 3D Printing 2014*, p. 38-39 (2014).

Mohammadi G. et al. "Meet seven makers who started their won companies, Faces of 3D printing", *Make: Ultimate Guide to 3D Printing 2014*, p. 25-27 (2014).

Newcomb T. "Foot Prints, Your Next Pair of Sneakers Will Be Printed to Order", *Popular Science*, p. 22, Jul. 2013.

P.J. De Jong J. "Innovation Lessons From 3-D Printing", *MIT Sloan Management Review*, Winter 2013, vol. 54, No. 2, p. 43-52 (2013).

Royte E. "The Printed World, 3-D Printing Promises a Factory in Every Home and a Whole Lot More", *Smithsonian*, May 2013, p. 50-57 (2013).

Stultz M. "Metal Madness; Move past plastic—use your 3D printer to cast objects in metal", *Make: Ultimate Guide to 3D Printing 2014*, p. 48-49 (2014).

3D Printing Forum, 3D Print Board, Kudo3D Titan1, Same Technology as Form 1?, May 30, 2014.

3DSYSTEMS, Projet 1200, Micro-SLA, Low-Cost Professional 3D Printer, 2013, 2 pages.

3DSYSTEMS, V-Flash, Personal 3D Printer, 2011, 2 pages.

B9Creator, Topic: PDMS and VAT, Feb. 19, 2013, 3 pages.

B9Creator, Topic: PDMS replacement advice sough: thanks in advance, Dec. 12, 2012, 2 pages.

B9Creator, Topic: Resin Technology/Discssion, Nov. 30, 2012, 5 pages.

BASF, The Chemical Company, Photoacid Generator Selection Guide for the Electronics Industry and Energy Curable Coatings, 2010, 3 pages.

Dendukuri et al. "Continuous-flow lithography for high-throughput microparticle synthesis", *Nature Materials*, vol. 5, May 2006, 365-369.

Dendukuri et al. "Modeling of Oxygen-Inhibited Free Radical Photopolymerization in a PDMS Microfluidic Device", *Macromolecules*, 2008, 41:8547-8556.

Dendukuri et al. "Stop-flow lithography in a microfluidic device", *The Royal Society of Chemistry, Lab on a Chip*, 2007, 7:818-828.

Dendukuri et al. "The Synthesis and Assembly of Polymeric Microparticles Using Microfluidics", *Adv. Mater.* 2009, 21:4071-4086.

Deutsch S., "3D Printer Prizefight: Makerbot Replicator 2 vs. Formlabs Form 1", *Popular Mechanics*, Nov. 14, 2012, 7 pages.

International Search Report and Written Opinion Corresponding to International Application No. PCT/US2014/015486; Date of Mailing: Sep. 30, 2014; 10 Pages.

International Search Report and Written Opinion Corresponding to International Application No. PCT/US2014/015497; Date of Mailing: Sep. 24, 2014; 10 Pages.

International Search Report and Written Opinion Corresponding to International Application No. PCT/US2014/015506; Date of Mailing: Oct. 13, 2014; 10 Pages.

Kickstarter, FORM 1: An affordable, professional 3D printer, by Formlabs, Oct. 26, 2012, 13 pages.

Kudo3D, The Titan 1, High Performance DLP SLA 3D Printer, 2014, 5 pages.

Lemoncurry, Open Source UV Photopolymer DLP 3D Printer, Apr. 30, 2012, 7 pages.

Lemoncurry, Open Source UV Photopolymer DLP 3D Printer, Mar. 4, 2013, 10 pages.

Titsch M. "Kudo3D's Titan 1 Approaches $400K on Kickstarter", Jun. 5, 2014, 4 pages.

Third Party Submission Submitted on May 26, 2015; 6 Pages.

Jariwala et al. "Exposure controlled projection lithography for microlens fabrication", *Proc. SPIE 8249, Advanced Fabrication Technologies for Micro/Nano Optics and Photonics* V. 824917, Feb. 9, 2012.

Jariwala et al. "Real-Time Interferometric Monitoring System for Exposure Controlled Projection Lithography", Solid Freeform Fabrication Symposium, University of Texas, 2011.

Jeong et al. "UV-assisted capillary force lithography for engineering biomimetic multiscale hierarchical structures: From lotus leaf to gecko foot hairs", *Nanoscale*, 2009, vol. 1:331-338, The Royal Society of Chemistry 2009.

Stern S.A. "The 'Barrer' Permeability Unit", *Journal of Polymer Science: Part A-2*, vol. 6, p. 1933-1934 (1968).

Thangawng et al. "UV Polymerization of Hydrodynamically Shaped Fibers", *ESI Lab on a Chip, Royal Society of Chemistry*, 2011.

U.S. Appl. No. 61/614,356, filed Mar. 22, 2012, Robert R. McLeod et al., "Liquid Deposition Photolithography", 28 pages.

Urness et al. "Liquid deposition photolithography for submicrometer resolution three-dimensional index structuring with large throughput", *Light: Science & Applications* (2013) 2, e56.

Urness et al. "Liquid deposition photolithography for sub-micron resolution three-dimensional index structuring with large throughput", Supplementary Information, 2013, 10 pages.

Urness et al. "Lithographic Fabrication of Multi-Layered Optical Data Storage", NLO/ISOM/ODS, 2011 OSA, OME2, 3 pages.

Urness, Adam C. (2013) *Liquid Deposition Photolithography for Efficient Three Dimensional Structuring*, Doctoral Dissertation, University of Colorado.

Yasuda H. "Permeability of Polymer Membranes to Dissolved Oxygen", *Journal of Polymer Science*, vol. 4, p. 1314-1316 (1966).

Dendukuri et al., Continuous-flow lithography for high-throughput microparticle synthesis, Nature Materials, vol. 5, pp. 365-369, May 2006, published online on Apr. 9, 2006, by Nature Publishing Group, UK.†

(56) References Cited

OTHER PUBLICATIONS

Dendukuri et al., Stop-flow lithography in a microfluidic device, Lab Chip, 2007, vol. 7, pp. 818-828, first published as an Advance Article on the web on May 21, 2007, by The Royal Society of Chemistry, UK.†

Dendukuri et al., Modeling of Oxygen-Inhibited Free Radical Photopolymerization in a PDMS Microfluidic Device, Macromolecules, 2008, vol. 41, No. 22, pp. 8547-8556, published on Oct. 21, 2008, by American Chemical Society, US.†

† cited by third party

CONTINUOUS LIQUID INTERPHASE PRINTING

RELATED APPLICATIONS

This application is a continuation of PCT Application No. PCT/US2014/015506, filed Feb. 10, 2014, which in turn claims the benefit of commonly owned U.S. Provisional Patent Application Ser. Nos. 61/919,903, filed Dec. 23, 2013; 61/865,841, filed Aug. 14, 2013 and 61/763,746, filed Feb. 12, 2013, the disclosures of which are incorporated by reference herein in their entirety.

FIELD OF THE INVENTION

The present invention concerns methods and apparatus for the fabrication of solid three-dimensional objects from liquid polymerizable materials.

BACKGROUND OF THE INVENTION

In conventional additive or three-dimensional fabrication techniques, construction of a three-dimensional object is performed in a step-wise or layer-by-layer manner. In particular, layer formation is performed through solidification of photo curable resin under the action of visible or UV light irradiation. Two techniques are known: one in which new layers are formed at the top surface of the growing object; the other in which new layers are formed at the bottom surface of the growing object.

If new layers are formed at the top surface of the growing object, then after each irradiation step the object under construction is lowered into the resin "pool," a new layer of resin is coated on top, and a new irradiation step takes place. An early example of such a technique is given in Hull, U.S. Pat. No. 5,236,637, at FIG. 3. A disadvantage of such "top down" techniques is the need to submerge the growing object in a (potentially deep) pool of liquid resin and reconstitute a precise overlayer of liquid resin.

If new layers are formed at the bottom of the growing object, then after each irradiation step the object under construction must be separated from the bottom plate in the fabrication well. An early example of such a technique is given in Hull, U.S. Pat. No. 5,236,637, at FIG. 4. While such "bottom up" techniques hold the potential to eliminate the need for a deep well in which the object is submerged by instead lifting the object out of a relatively shallow well or pool, a problem with such "bottom up" fabrication techniques, as commercially implemented, is that extreme care must be taken, and additional mechanical elements employed, when separating the solidified layer from the bottom plate due to physical and chemical interactions therebetween. For example, in U.S. Pat. No. 7,438,846, an elastic separation layer is used to achieve "non-destructive" separation of solidified material at the bottom construction plane. Other approaches, such as the B9Creator™ 3-dimensional printer marketed by B9Creations of Deadwood, S. Dak., USA, employ a sliding build plate. See, e.g., M. Joyce, US Patent App. 2013/0292862 and Y. Chen et al., US Patent App. 2013/0295212 (both Nov. 7, 2013); see also Y. Pan et al., *J. Manufacturing Sci. and Eng.* 134, 051011-1 (October 2012). Such approaches introduce a mechanical step that may complicate the apparatus, slow the method, and/or potentially distort the end product.

Continuous processes for producing a three-dimensional object are suggested at some length with respect to "top down" techniques in U.S. Pat. No. 7,892,474, but this reference does not explain how they may be implemented in "bottom up" systems in a manner non-destructive to the article being produced. Accordingly, there is a need for alternate methods and apparatus for three-dimensional fabrication that can obviate the need for mechanical separation steps in "bottom-up" fabrication.

SUMMARY OF THE INVENTION

Described herein are methods, systems and apparatus (including associated control methods, systems and apparatus), for the generally continuous production of a three-dimensional object. In these methods, systems and apparatus, the three-dimensional object is produced from a liquid interface. Hence they are sometimes referred to, for convenience and not for purposes of limitation, as "continuous liquid interphase printing." A schematic representation is given in FIG. 1 herein.

As discussed below, the interface is between first and second layers or zones of the same polymerizable liquid. The first layer or zone (sometimes also referred to as a "dead zone") contains an inhibitor of polymerization (at least in a polymerization-inhibiting amount); in the second layer or zone the inhibitor has been consumed (or has not otherwise been incorporated or penetrated therein) to the point where polymerization is no longer substantially inhibited. The first and second zones do not form a strict interface between one another but rather there is a gradient of composition that can also be described as forming an interphase between them as opposed to a sharp interface, as the phases are miscible with one another, and further create a (partially or fully overlapping) gradient of polymerization therebetween (and also between the three-dimensional object being fabricated, and the build surface through which the polymerizable liquid is irradiated). The three-dimensional object can be fabricated, grown or produced continuously from that gradient of polymerization (rather than fabricated layer-by-layer). As a result, the creation of fault or cleavage lines in the object being produced, which may occur in layer-by-layer techniques such as described in Y. Pan et al. or J. Joyce et al. (noted above), may be reduced or obviated. Of course, such fault or cleavage lines can be intentionally introduced when desired as discussed further below.

In some embodiments of continuous liquid interphase printing, the first layer or zone is provided immediately on top of, or in contact with, a build plate. The build plate is transparent to the irradiation which initiates the polymerization (e.g., patterned radiation), but the build plate is preferably semipermeable to the polymerization inhibitor and allows the inhibitor of polymerization (e.g., oxygen) to pass partly or fully therethrough (e.g., to continuously feed inhibitor to the "dead zone"). The build plate is preferably "fixed" or "stationary" in the sense that it need not slide, retract, rebound or the like to create separate or sequential steps (as in a layer-by-layer process). Of course, minor motion of the build plate in the x and/or y directions that does not unduly disrupt the gradient of polymerization, but still permits continuous polymerization from the liquid interface, may still be accommodated in some embodiments, as also discussed below.

Thus the present invention provides a method of forming a three-dimensional object, comprising: providing a carrier and an optically transparent member having a build surface, said carrier and said build surface defining a build region therebetween; filling said build region with a polymerizable liquid; irradiating said build region through said optically transparent member to form a solid polymer from said polymerizable liquid while concurrently advancing said carrier away from said build surface to form said three-dimensional object from said solid polymer, while also concurrently (i) continuously maintaining a dead zone of polymerizable liquid in contact with said build surface, and (ii) continuously maintaining a gradient of polymerization zone between said dead zone and said solid polymer and in contact with each thereof, said gradient of polymerization zone comprising said polymerizable liquid in partially cured form (e.g., so that the formation of fault or cleavage lines between layers of solid polymer in said three-dimensional object is reduced). In some embodiments, the optically transparent member comprises a semipermeable member, and said continuously maintaining a dead zone is carried out by feeding an inhibitor of polymerization through said optically transparent member, thereby creating a gradient of inhibitor in said dead zone and optionally in at least a portion of said gradient of polymerization zone; in other embodiments, the optically transparent member comprises a semipermeable member, and is configured to contain a sufficient amount (or "pool") of inhibitor to continuously maintain the dead zone for a sufficient length of time, to produce the article being fabricated without additional feeding of inhibitor during the process (which "pool" may be replenished or recharged between production runs). In some embodiments, the optically transparent member is comprised of a semipermeable fluoropolymer, a rigid gas-permeable polymer, porous glass, or a combination thereof. In some embodiments, the irradiating step is carried out with a two-dimensional radiation pattern projected into said build region, wherein said pattern varies over time while said concurrently advancing step continues for a time sufficient to form said three-dimensional object (i.e., during which time said gradient of polymerization zone is maintained).

While the dead zone and the gradient of polymerization zone do not have a strict boundary therebetween (in those locations where the two meet), the thickness of the gradient of polymerization zone is in some embodiments at least as great as the thickness of the dead zone. Thus, in some embodiments, the dead zone has a thickness of from 0.01, 0.1, 1, 2, or 10 microns up to 100, 200 or 400 microns, or more, and/or said gradient of polymerization zone and said dead zone together have a thickness of from 1 or 2 microns up to 400, 600, or 1000 microns, or more. In some embodiments, the gradient of polymerization zone is maintained (while polymerizing steps continue) for a time of at least 5, 10, 15, 20 or 30 seconds, up to 5, 10, 15 or 20 minutes or more, or until completion of the three-dimensional product.

The method may further comprise the step of disrupting said gradient of polymerization zone for a time sufficient to form a cleavage line in said three-dimensional object (e.g., at a predetermined desired location for intentional cleavage, or at a location in said object where prevention of cleavage or reduction of cleavage is non-critical), and then reinstating said gradient of polymerization zone (e.g. by pausing, and resuming, the advancing step, increasing, then decreasing, the intensity of irradiation, and combinations thereof).

The method may further comprise heating said polymerizable liquid as it is supplied to the build region and/or within the build region (e.g., by an amount as given in the Examples below) to reduce the viscosity thereof in the build region (e.g., by an amount as given in the Examples below).

The method may be carried out and the apparatus implemented wherein said carrier has at least one channel formed therein, and said filling step is carried out by passing or forcing said polymerizable liquid into said build region through said at least one channel (e.g., wherein said carrier has a plurality of channels formed therein, and wherein different polymerizable liquids are forced through different ones of said plurality of channels; e.g., further comprising concurrently forming at least one, or a plurality of, external feed conduits separate from said object, each of said at least one feed conduits in fluid communication with a channel in said carrier, to supply at least one, or a plurality of different, polymerizable liquids from said carrier to said build zone). In some embodiments, the semipermeable member has a thickness of from 0.1 or 1 millimeters to 10 or 100 millimeters; and/or said semipermeable member has a permeability to oxygen of at least 10 Barrers.

A particular aspect of the present invention is, accordingly, a method of forming a three-dimensional object, comprising: providing a carrier and an optically transparent member having a build surface, the carrier and the build surface defining a build region therebetween; filling the build region with a polymerizable liquid; irradiating the build region through the optically transparent member to form a solid polymer from the polymerizable liquid while concurrently advancing the carrier away from the build surface to form the three-dimensional object from the solid polymer, while also concurrently: (i) continuously maintaining a dead zone of polymerizable liquid in contact with the build surface, and (ii) continuously maintaining a gradient of polymerization zone between the dead zone and the solid polymer and in contact with each thereof, the gradient of polymerization zone comprising the polymerizable liquid in partially cured form.

In some embodiments, the optically transparent member comprises a semipermeable member, and the continuously maintaining a dead zone is carried out by feeding an inhibitor of polymerization through the optically transparent member, thereby creating a gradient of inhibitor in the dead zone and optionally in at least a portion of the gradient of polymerization zone.

In some embodiments of the foregoing, the optically transparent member is comprised of a semipermeable fluoropolymer, a rigid gas-permeable polymer, porous glass, or a combination thereof.

In some embodiments of the foregoing, the irradiating step is carried out by maskless photolithography.

In some embodiments of the foregoing, the irradiating step is carried out with a two-dimensional radiation pattern projected into the build region, wherein the pattern varies over time while the concurrently advancing step continues for a time sufficient to form the three-dimensional object.

In some embodiments of the foregoing, the gradient of polymerization zone and the dead zone together have a thickness of from 1 to 1000 microns.

In some embodiments of the foregoing, the gradient of polymerization zone is maintained for a time of at least 5 seconds.

In some embodiments of the foregoing, the method further comprises the step of disrupting the gradient of polymerization zone for a time sufficient to form a cleavage line in the three-dimensional object.

In some embodiments of the foregoing, the method further comprises heating the polymerizable liquid to reduce the viscosity thereof in the build region.

In some embodiments of the foregoing, the carrier has at least one channel formed therein, and the filling step is carried out by passing or forcing the polymerizable liquid into the build region through the at least one channel.

In some embodiments of the foregoing, the semipermeable member has a thickness of from 0.1 to 100 millimeters; and/or wherein the semipermeable member has a permeability to oxygen of at least $7.5 \times 10^{-17}$ $m^2 s^{-1} Pa^{-1}$ (10 Barrers); and/or wherein the semipermeable member is formed of a semipermeable fluoropolymer, a rigid gas-permeable polymer, porous glass, or a combination thereof.

In some embodiments of the foregoing, the irradiating step is carried out with actinic radiation.

In some embodiments of the foregoing, the concurrently advancing is carried out at a cumulative rate of at least 0.1, 1, 10, 100 or 1000 microns per second.

In some embodiments of the foregoing, the carrier has a soluble sacrificial layer thereon, and the three-dimensional object is formed on the soluble sacrificial layer.

In some embodiments of the foregoing, the total surface area of the build region occupies at least seventy percent of the total surface area of the build surface; and/or wherein lateral movement of the carrier and object in any direction is not more than thirty percent of the width of the build region in the corresponding direction.

In some embodiments of the foregoing, the polymerizable liquid comprises a free radical polymerizable liquid and the inhibitor comprises oxygen.

In some embodiments of the foregoing, the polymerizable liquid comprises an acid-catalyzed or cationically polymerizable liquid, and the inhibitor comprises a base.

In some embodiments of the foregoing, the build surface is substantially fixed or stationary.

A further particular aspect of the invention is an apparatus for forming a three-dimensional object from a polymerizable liquid, comprising: (a) a support; (b) a carrier operatively associated with the support, on which carrier the three-dimensional object is formed; (c) an optically transparent member having a build surface, with the build surface and the carrier defining a build region therebetween; (d) a liquid polymer supply operatively associated with the build surface and configured to supply liquid polymer into the build region for solidification polymerization; (e) a radiation source configured to irradiate the build region through the optically transparent member to form a solid polymer from the polymerizable liquid; (f) controller operatively associated with the carrier and the radiation source for advancing the carrier away from the build surface to form the three-dimensional object from the solid polymer, while also concurrently: (i) continuously maintaining a dead zone of polymerizable liquid in contact with the build surface, and (ii) continuously maintaining a gradient of polymerization zone between the dead zone and the solid polymer and in contact with each thereof, the gradient of polymerization zone comprising the polymerizable liquid in partially cured form.

In some embodiments of the foregoing, the carrier has at least one channel formed therein, configured for supply of the polymerizable liquid into the build region through the at least one channel.

In some embodiments of the foregoing, the carrier has a plurality of channels formed therein, configured for supply of different polymerizable liquids through different ones of the plurality of channels.

In some embodiments of the foregoing, there are provided at least one, or a plurality of, external feed conduits separate from the object (e.g., fabricated in the course thereof or concurrently therewith), each of the at least one feed conduits in fluid communication with a channel in the carrier, configured for supply of at least one, or a plurality of different, polymerizable liquids from the carrier to the build zone.

In some embodiments, the build plate is substantially fixed or stationary.

In some embodiments, the source of polymerization inhibitor is a reservoir of polymerization inhibitor within the semipermeable member.

In some embodiments, the semipermeable member further comprises a feed surface separate from the build surface.

In some embodiments, the feed surface is in fluid contact with a polymerization inhibitor so as to provide the source of polymerization inhibitor.

In some embodiments, the apparatus further comprises a heater operatively associated with the build plate and/or the liquid polymer supply, the heater configured to heat polymerizable liquid in or supplied to the build region.

In some embodiments, the apparatus further comprises a cooler operatively associated with the build plate and configured to cool polymerizable liquid in the build region.

In some embodiments, the semipermeable member comprises a top surface portion, a bottom surface portion, and an edge surface portion; the build surface is on the top surface portion; and the feed surface is on at least one of the top surface portion, the bottom surface portion, and the edge surface portion.

In some embodiments, the apparatus further comprises a pressure source operatively associated with the liquid polymer supply.

In some embodiments, the radiation source comprises a light source.

In some embodiments, the apparatus comprises a spatial light modulation array operatively associated with the radiation source and the controller and configured to carry out irradiation of the polymerizable liquid by maskless photolithography.

In some embodiments, the carrier comprises a plate, post, web, film, reel, or combination thereof operatively associated with at least one actuator.

In some embodiments, the carrier comprises a drive, the drive and the controller configured to advance the carrier unidirectionally away from the build surface.

In some embodiments, the carrier has a soluble sacrificial layer thereon, and the three-dimensional object is formed on the soluble sacrificial layer.

In the B9Creator™ 3-dimensional printer, a polydimethylsiloxane (PDMS) coating is applied to the sliding build surface. The PDMS coating is said to absorb oxygen and create a thin lubricating film of unpolymerized resin through its action as a polymerization inhibitor. However, the PDMS coated build surface is directly replenished with oxygen by mechanically moving (sliding) the surface from beneath the growing object, while wiping unpolymerized resin therefrom with a wiper blade, and then returning it to its previous position beneath the growing object. While in some embodiments auxiliary means of providing an inhibitor such as oxygen are provided (e.g., a compressor to associated channels), the process still employs a layer-by-layer approach with sliding and wiping of the surface. Since the PDMS coating may be swollen by the resin, this swelling, along with these mechanical steps, may result in tearing of or damage to the PDMS coating.

Non-limiting examples and specific embodiments of the present invention are explained in greater detail in the drawings herein and the specification set forth below. The disclosure of all United States Patent references cited herein are to be incorporated herein by reference in their entirety.

BRIEF DESCRIPTION OF THE DRAWINGS

FIG. 5B illustrates the embodiment of FIG. 5A, with application of UV radiation.

FIG. 5E illustrates the embodiment of FIG. 5D, with application of UV radiation.

FIG. 5H illustrates the embodiment of FIG. 5G, with application of UV radiation.

FIG. 6C shows the structure of one sample of FIG. 6B being exposed to UV radiation immediately after being taken from the nitrogen environment.

FIG. 6E shows the structure of a second sample of FIG. 6B being exposed to UV radiation, ten minutes after being taken from the nitrogen environment, during which time the sample was exposed to an atmosphere environment.

DETAILED DESCRIPTION OF ILLUSTRATIVE EMBODIMENTS

Figure 1:
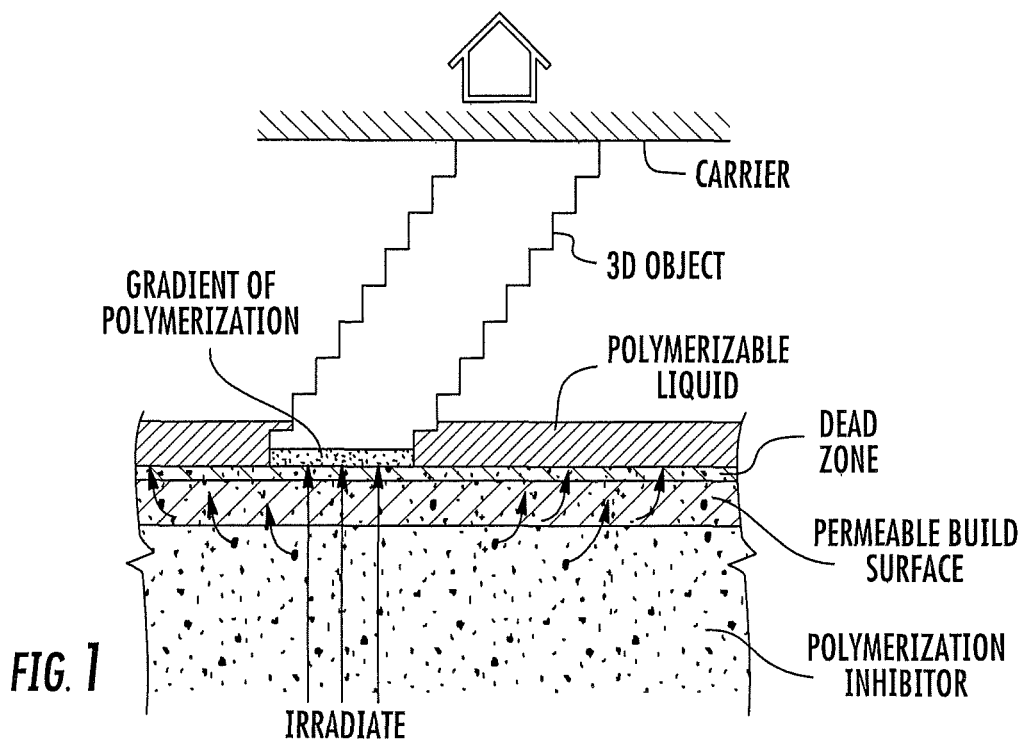
FIG. 1 is a schematic illustration of one embodiment of a method of the present invention.

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

Like numbers refer to like elements throughout. In the figures, the thickness of certain lines, layers, components, elements or features may be exaggerated for clarity. Where used, broken lines illustrate optional features or operations unless specified otherwise.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" or "comprising," when used in this specification, specify the presence of stated features, integers, steps, operations, elements components and/or groups or combinations thereof, but do not preclude the presence or addition of one or more other features, integers, steps, operations, elements, components and/or groups or combinations thereof.

As used herein, the term "and/or" includes any and all possible combinations or one or more of the associated listed items, as well as the lack of combinations when interpreted in the alternative ("or").

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with and/or contacting the other element or intervening elements can also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature can have portions that overlap or underlie the adjacent feature.

Spatially relative terms, such as "under," "below," "lower," "over," "upper" and the like, may be used herein for ease of description to describe an element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus the exemplary term "under" can encompass both an orientation of over and under. The device may otherwise be oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only, unless specifically indicated otherwise.

It will be understood that, although the terms first, second, etc., may be used herein to describe various elements, components, regions, layers and/or sections, these elements, components, regions, layers and/or sections should not be limited by these terms. Rather, these terms are only used to distinguish one element, component, region, layer and/or section, from another element, component, region, layer and/or section. Thus, a first element, component, region, layer or section discussed herein could be termed a second element, component, region, layer or section without departing from the teachings of the present invention. The sequence of operations (or steps) is not limited to the order presented in the claims or figures unless specifically indicated otherwise.

1. Polymerizable Liquids.

Any suitable polymerizable liquid can be used to enable the present invention. The liquid (sometimes also referred to as "liquid resin" "ink," or simply "resin" herein) can include a monomer, particularly photopolymerizable and/or free radical polymerizable monomers, and a suitable initiator such as a free radical initiator, and combinations thereof. Examples include, but are not limited to, acrylics, methacrylics, acrylamides, styrenics, olefins, halogenated olefins, cyclic alkenes, maleic anhydride, alkenes, alkynes, carbon monoxide, functionalized oligomers, multifunctional cute site monomers, functionalized PEGs, etc., including combinations thereof. Examples of liquid resins, monomers and initiators include but are not limited to those set forth in U.S. Pat. Nos. 8,232, 043; 8,119,214; 7,935,476; 7,767,728; 7,649,029; WO 2012129968 A1; CN 102715751 A; JP 2012210408A.

Acid catalyzed polymerizable liquids. While in some embodiments as noted above the polymerizable liquid comprises a free radical polymerizable liquid (in which case an inhibitor may be oxygen as described below), in other embodiments the polymerizable liquid comprises an acid catalyzed, or cationically polymerized, polymerizable liquid. In such embodiments the polymerizable liquid comprises monomers contain groups suitable for acid catalysis, such as epoxide groups, vinyl ether groups, etc. Thus suitable monomers include olefins such as methoxyethene, 4-methoxystyrene, styrene, 2-methylprop-1-ene, 1,3-butadiene, etc.; heterocycloic monomers (including lactones, lactams, and cyclic amines) such as oxirane, thietane, tetrahydrofuran, oxazoline, 1,3, dioxepane, oxetan-2-one, etc., and combinations thereof. A suitable (generally ionic or non-ionic) photoacid generator (PAG) is included in the acid catalyzed polymerizable liquid, examples of which include, but are not limited to onium salts, sulfonium and iodonium salts, etc., such as diphenyl iodide hexafluorophosphate, diphenyl iodide hexafluoroarsenate, diphenyl iodide hexafluoroantimonate, diphenyl p-methoxyphenyl triflate, diphenyl p-tolueneyl triflate, diphenyl p-isobutylphenyl triflate, diphenyl p-tert-butylphenyl triflate, triphenylsulfonium hexafluorophosphate, triphenylsulfonium hexafluoroarsenate, triphenylsulfonium hexafluoroantimonate, triphenylsulfonium triflate, dibutylnaphthylsulfonium triflate, etc., including mixtures thereof. See, e.g., U.S. Pat. Nos. 7,824,839; 7,550, 246; 7,534,844; 6,692,891; 5,374,500; and 5,017,461; see also *Photoacid Generator Selection Guide for the electronics industry and energy curable coatings* (BASF 2010).

Hydrogels. In some embodiments suitable resins includes photocurable hydrogels like poly(ethylene glycols) (PEG) and gelatins. PEG hydrogels have been used to deliver a variety of biologicals, including Growth factors; however, a great challenge facing PEG hydrogels crosslinked by chain growth polymerizations is the potential for irreversible protein damage. Conditions to maximize release of the biologicals from photopolymerized PEG diacrylate hydrogels can be enhanced by inclusion of affinity binding peptide sequences in the monomer resin solutions, prior to photopolymerization allowing sustained delivery. Gelatin is a biopolymer frequently used in food, cosmetic, pharmaceutical and photographic industries. It is obtained by thermal denaturation or chemical and physical degradation of collagen. There are three kinds of gelatin, including those found in animals, fish and humans. Gelatin from the skin of cold water fish is considered safe to use in pharmaceutical applications. UV or visible light can be used to crosslink appropriately modified gelatin. Methods for crosslinking gelatin include cure derivatives from dyes such as Rose Bengal.

Photocurable silicone resins. A suitable resin includes photocurable silicones. UV cure silicone rubber, such as Siliopren™ UV Cure Silicone Rubber can be used as can LOCTITE™ Cure Silicone adhesives sealants. Applications include optical instruments, medical and surgical equipment, exterior lighting and enclosures, electrical connectors/sensors, fiber optics and gaskets.

Biodegradable resins. Biodegradable resins are particularly important for implantable devices to deliver drugs or for temporary performance applications, like biodegradable screws and stents (U.S. Pat. Nos. 7,919,162; 6,932,930). Biodegradable copolymers of lactic acid and glycolic acid (PLGA) can be dissolved in PEG dimethacrylate to yield a transparent resin suitable for use. Polycaprolactone and PLGA oligomers can be functionalized with acrylic or methacrylic groups to allow them to be effective resins for use.

Photocurable polyurethanes. A particularly useful resin is photocurable polyurethanes. A photopolymerizable polyurethane composition comprising (1) a polyurethane based on an aliphatic diisocyanate, poly(hexamethylene isophthalate glycol) and, optionally, 1,4-butanediol; (2) a polyfunctional acrylic ester; (3) a photoinitiator; and (4) an anti-oxidant, can be formulated so that it provides a hard, abrasion-resistant, and stain-resistant material (U.S. Pat. No. 4,337,130). Photocurable thermoplastic polyurethane elastomers incorporate photoreactive diacetylene diols as chain extenders.

High performance resins. In some embodiments, high performance resins are used. Such high performance resins may sometimes require the use of heating to melt and/or reduce the viscosity thereof, as noted above and discussed further below. Examples of such resins include, but are not limited to, resins for those materials sometimes referred to as liquid crystalline polymers of esters, ester-imide, and ester-amide oligomers, as described in U.S. Pat. Nos. 7,507,784; 6,939,940. Since such resins are sometimes employed as high-temperature thermoset resins, in the present invention they further comprise a suitable photoinitiator such as benzophenone, anthraquinone, amd fluoroenone initiators (including derivatives thereof), to initiate cross-linking on irradiation, as discussed further below.

Additional example resins. Particularly useful resins for dental applications include EnvisionTEC's Clear Guide, EnvisionTEC's E-Denstone Material. Particularly useful resins for hearing aid industries include EnvisionTEC's e-Shell 300 Series of resins. Particularly useful resins include EnvisionTEC's HTM140IV High Temperature Mold Material for use directly with vulcanized rubber in molding/casting applications. A particularly useful material for making tough and stiff parts includes EnvisionTEC's RC31 resin. A particulary useful resin for investment casting applications includes EnvisionTEC's Easy Cast EC500.

Additional resin ingredients. The liquid resin or polymerizable material can have solid particles suspended or dispersed therein. Any suitable solid particle can be used, depending upon the end product being fabricated. The particles can be metallic, organic/polymeric, inorganic, or composites or mixtures thereof. The particles can be nonconductive, semi-conductive, or conductive (including metallic and non-metallic or polymer conductors); and the particles can be magnetic, ferromagnetic, paramagnetic, or nonmagnetic. The particles can be of any suitable shape, including spherical, elliptical, cylindrical, etc. The particles can comprise an active agent or detectable compound as described below, though these may also be provided dissolved solubilized in the liquid resin as also discussed below. For example, magnetic or paramagnetic particles or nanoparticles can be employed.

The liquid resin can have additional ingredients solubilized therein, including pigments, dyes, active compounds or pharmaceutical compounds, detectable compounds (e.g., fluorescent, phosphorescent, radioactive), etc., again depending upon the particular purpose of the product being fabricated. Examples of such additional ingredients include, but are not limited to, proteins, peptides, nucleic acids (DNA, RNA) such as siRNA, sugars, small organic compounds (drugs and drug-like compounds), etc., including combinations thereof.

Inhibitors of polymerization. Inhibitors or polymerization inhibitors for use in the present invention may be in the form of a liquid or a gas. In some embodiments, gas inhibitors are preferred. The specific inhibitor will depend upon the monomer being polymerized and the polymerization reaction. For free radical polymerization monomers, the inhibitor can conveniently be oxygen, which can be provided in the form of a gas such as air, a gas enriched in oxygen (optionally but in some embodiments preferably containing additional inert gases to reduce combustibility thereof), or in some embodiments pure oxygen gas. In alternate embodiments, such as where the monomer is polymerized by photoacid generator initiator, the inhibitor can be a base such as ammonia, trace amines (e.g. methyl amine, ethyl amine, di and trialkyl amines such as dimethyl amine, diethyl amine, trimethyl amine, triethyl amine, etc.), or carbon dioxide, including mixtures or combinations thereof.

Polymerizable liquids carrying live cells. In some embodiments, the polymerizable liquid may carry live cells as "particles" therein. Such polymerizable liquids are generally aqueous, and may be oxygenated, and may be considered as "emulsions" where the live cells are the discrete phase. Suitable live cells may be plant cells (e.g., monocot, dicot), animal cells (e.g., mammalian, avian, amphibian, reptile cells), microbial cells (e.g., prokaryote, eukaryote, protozoal, etc.), etc. The cells may be of differentiated cells from or corresponding to any type of tissue (e.g., blood, cartilage, bone, muscle, endocrine gland, exocrine gland, epithelial, endothelial, etc.), or may be undifferentiated cells such as stem cells or progenitor cells. In such embodiments the polymerizable liquid can be one that forms a hydrogel, including but not limited to those described in U.S. Pat. Nos. 7,651,683; 7,651,682; 7,556,490; 6,602,975; 5,836,313; etc.

2. Apparatus.

Figure 2:
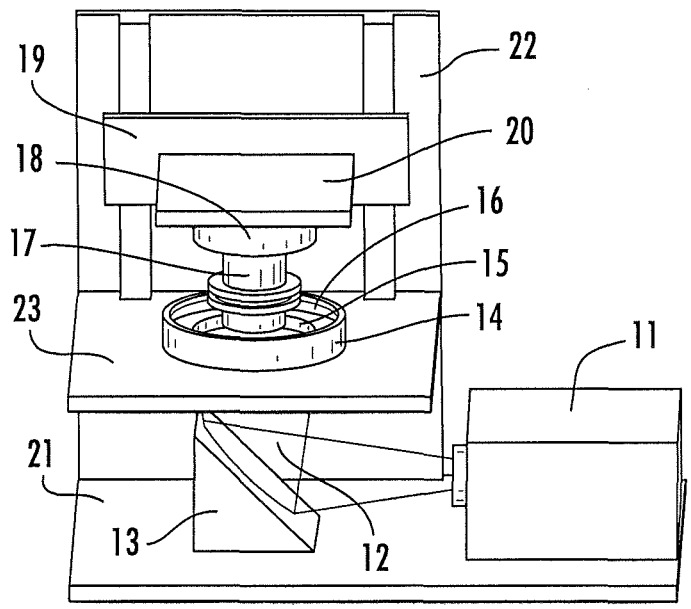
FIG. 2 is a perspective view of one embodiment of an apparatus of the present invention.

A non-limiting embodiment of an apparatus of the invention is shown in FIG. 2. It comprises a radiation source 11 such as a digital light processor (DLP) providing electromagnetic radiation 12 which though reflective mirror 13 illuminates a build chamber defined by wall 14 and a rigid build plate 15 forming the bottom of the build chamber, which build chamber is filled with liquid resin 16. The bottom of the chamber 15 is constructed of rigid build plate comprising a rigid semipermeable member as discussed further below. The top of the object under construction 17 is attached to a carrier 18. The carrier is driven in the vertical direction by linear stage 19, although alternate structures can be used as discussed below.

A liquid resin reservoir, tubing, pumps liquid level sensors and/or valves can be included to replenish the pool of liquid resin in the build chamber (not shown for clarity) though in some embodiments a simple gravity feed may be employed. Drives/actuators for the carrier or linear stage, along with associated wiring, can be included in accordance with known techniques (again not shown for clarity). The drives/actuators, radiation source, and in some embodiments pumps and liquid level sensors can all be operatively associated with a suitable controller, again in accordance with known techniques.

Build plates 15 used to carry out the present invention generally comprise or consist of a (typically rigid or solid, stationary, and/or fixed) semipermeable (or gas permeable) member, alone or in combination with one or more additional supporting substrates (e.g., clamps and tensioning members to rigidify an otherwise flexible semipermeable material). The rigid semipermeable member can be made of any suitable material that is optically transparent at the relevant wavelengths (or otherwise transparent to the radiation source, whether or not it is visually transparent as perceived by the human eye—i.e., an optically transparent window may in some embodiments be visually opaque), including but not limited to porous or microporous glass, and the rigid gas permeable polymers used for the manufacture of rigid gas permeable contact lenses. See, e.g., Norman G. Gaylord, U.S. Pat. No. RE31,406; see also U.S. Pat. Nos. 7,862,176; 7,344,731; 7,097,302; 5,349,394; 5,310,571; 5,162,469; 5,141,665; 5,070,170; 4,923,906; and 4,845,089. In some embodiments such materials are characterized as glassy and/or amorphous polymers and/or substantially crosslinked that they are essentially non-swellable. Preferably the rigid semipermeable member is formed of a material that does not swell when contacted to the liquid resin or material to be polymerized (i.e., is "non-swellable"). Suitable materials for the rigid semipermeable member include rigid amorphous fluoropolymers, such as those described in U.S. Pat. Nos. 5,308,685 and 5,051,115. For example, such fluoropolymers are particularly useful over silicones that would potentially swell when used in conjunction with organic liquid resin inks to be polymerized. For some liquid resin inks, such as more aqueous-based monomeric systems and/or some polymeric resin ink systems that have low swelling tendencies, silicone based window materials maybe suitable. The solubility or permeability of organic liquid resin inks can be dramatically decreased by a number of known parameters including increasing the crosslink density of the window material or increasing the molecular weight of the liquid resin ink. In some embodiments the build plate may be formed from a thin film or sheet of material which is flexible when separated from the apparatus of the invention, but which is clamped and tensioned when installed in the apparatus (e.g., with a tensioning ring) so that it is rendered rigid in the apparatus. Particular materials include TEFLON AF® fluoropolymers, commercially available from DuPont. Additional materials include perfluoropolyether polymers such as described in U.S. Pat. Nos. 8,268,446; 8,263,129; 8,158,728; and 7,435,495.

It will be appreciated that essentially all solid materials, and most of those described above, have some inherent "flex" even though they may be considered "rigid," depending on factors such as the shape and thickness thereof and environmental factors such as the pressure and temperature to which they are subjected. In addition, the terms "stationary" or "fixed" with respect to the build plate is intended to mean that no mechanical interruption of the process occurs, or no mechanism or structure for mechanical interruption of the process (as in a layer-by-layer method or apparatus) is provided, even if a mechanism for incremental adjustment of the build plate (for example, adjustment that does not lead to or cause collapse of the gradient of polymerization zone) is provided).

The semipermeable member typically comprises a top surface portion, a bottom surface portion, and an edge surface portion. The build surface is on the top surface portion; and the feed surface may be on one, two, or all three of the top surface portion, the bottom surface portion, and/or the edge surface portion. In the embodiment illustrated in FIG. 2 the feed surface is on the bottom surface portion, but alternate configurations where the feed surface is provided on an edge, and/or on the top surface portion (close to but separate or spaced away from the build surface) can be implemented with routine skill.

The semipermeable member has, in some embodiments, a thickness of from 0.01, 0.1 or 1 millimeters to 10 or 100 millimeters, or more (depending upon the size of the item being fabricated, whether or not it is laminated to or in contact with an additional supporting plate such as glass, etc., as discussed further below.

The permeability of the semipermeable member to the polymerization inhibitor will depend upon conditions such as the pressure of the atmosphere and/or inhibitor, the choice of inhibitor, the rate or speed of fabrication, etc. In general, when the inhibitor is oxygen, the permeability of the semipermeable member to oxygen may be from 10 or 20 Barrers, up to 1000 or 2000 Barrers, or more. For example, a semipermeable member with a permeability of 10 Barrers used with a pure oxygen, or highly enriched oxygen, atmosphere under a pressure of 150 PSI may perform substantially the same as a semipermeable member with a permeability of 500 Barrers when the oxygen is supplied from the ambient atmosphere under atmospheric conditions.

Thus, the semipermeable member may comprise a flexible polymer film (having any suitable thickness, e.g., from 0.001, 0.01, 0.1 or 1 millimeters to 5, 10, or 100 millimeters, or more), and the build plate may further comprise a tensioning member (e.g., a peripheral clamp and an operatively associated strain member or stretching member, as in a "drum head"; a plurality of peripheral clamps, etc., including combinations thereof) connected to the polymer film and to fix and rigidify the film (e.g., at least sufficiently so that the film does not stick to the object as the object is advanced and resiliently or elastically rebound therefrom). The film has a top surface and a bottom surface, with the build surface on the top surface and the feed surface preferably on the bottom surface. In other embodiments, the semipermeable member comprises: (i) a polymer film layer (having any suitable thickness, e.g., from 0.001, 0.01, 0.1 or 1 millimeters to 5, 10 or 100 millimeters, or more), having a top surface positioned for contacting said polymerizable liquid and a bottom surface, and (ii) a rigid, gas permeable, optically transparent supporting member (having any suitable thickness, e.g., from 0.01, 0.1 or 1 millimeters to 10, 100, or 200 millimeters, or more), contacting said film layer bottom surface. The supporting member has a top surface contacting the film layer bottom surface, and the supporting member has a bottom surface which may serve as the feed surface for the polymerization inhibitor. Any suitable materials that are semipermeable (that is, permeable to the polymerization inhibitor) may be used. For example, the polymer film or polymer film layer may, for example, be a fluoropolymer film, such as an amorphous thermoplastic fluoropolymer like TEFLON AF1600™ or TEFLON AF 2400™ fluoropolymer films, or perfluoropolyether (PFPE), particularly a crosslinked PFPE film, or a crosslinked silicone polymer film. The supporting member comprises a silicone or crosslinked silicone polymer member such as a polydmethylxiloxane member, a rigid gas permeable polymer member, or a porous or microporous glass member. Films can be laminated or clamped directly to the rigid supporting member without adhesive (e.g., using PFPE and PDMS materials), or silane coupling agents that react with the upper surface of a PDMS layer can be utilized to adhere to the first polymer film layer. UV-curable, acrylate-functional silicones can also be used as a tie layer between UV-curable PFPEs and rigid PDMS supporting layers.

As noted above, while in some embodiments the semipermeable member allows inhibitor to pass therethrough, it can simply be configured to contain a sufficient amount (or "pool") of inhibitor to continuously maintain the dead zone for a sufficient length of time, to produce the article being fabricated without additional feeding of inhibitor during the process (which "pool" may be replenished or recharged between production runs). The size and internal volume of the member can be configured as appropriate for the particular article being fabricated to contain a sufficient pool of inhibitor.

When configured for placement in the apparatus, the carrier defines a "build region" on the build surface, within the total area of the build surface. Because lateral "throw" (e.g., in the X and/or Y directions) is not required in the present invention to break adhesion between successive layers, as in the Joyce and Chen devices noted previously, the area of the build region within the build surface may be maximized (or conversely, the area of the build surface not devoted to the build region may be minimized). Hence in some embodiments, the total surface area of the build region can occupy at least fifty, sixty, seventy, eighty, or ninety percent of the total surface area of the build surface.

As shown in FIG. 2, the various components are mounted on a support or frame assembly 20. While the particular design of the support or frame assembly is not critical and can assume numerous configurations, in the illustrated embodiment it is comprised of a base 21 to which the radiation source 11 is securely or rigidly attached, a vertical member 22 to which the linear stage is operatively associated, and a horizontal table 23 to which wall 14 is removably or securely attached (or on which the wall is placed), and with the build plate rigidly fixed, either permanently or removably, to form the build chamber as described above.

Figure 3A:
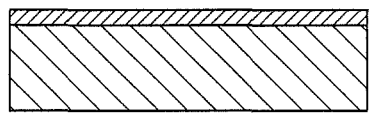
FIG. 3A provides a side sectional view of a first alternate embodiment of a rigid build plate for use in the present invention.
Figure 3B:
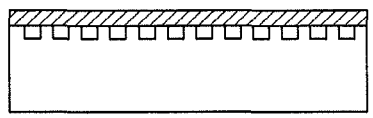
FIG. 3B provides a side sectional view of a second alternate embodiment of a rigid build plate for use in the present invention.

As noted above, the build plate can consist of a single unitary and integral piece of a rigid semipermeable member, or can comprise additional materials. For example, as shown in FIG. 3A, a porous or microporous glass can be laminated or fixed to a rigid semipermeable material. Or, as shown in FIG. 3B, a semipermeable member as an upper portion can be fixed to a transparent lower member having purging channels formed therein for feeding gas carrying the polymerization inhibitor to the semipermeable member (through which it passes to the build surface to facilitate the formation of a release layer of unpolymerized liquid material, as noted above and below). Such purge channels may extend fully or partially through the base plate: For example, the purge channels may extend partially into the base plate, but then end in the region directly underlying the build surface to avoid introduction of distortion. Specific geometries will depend upon whether the feed surface for the inhibitor into the semipermeable member is located on the same side or opposite side as the build surface, on an edge portion thereof, or a combination of several thereof.

Any suitable radiation source (or combination of sources) can be used, depending upon the particular resin employed, including electron beam and ionizing radiation sources. In a preferred embodiment the radiation source is an actinic radiation source, such as one or more light sources, and in particular one or more ultraviolet light sources. Any suitable light source can be used, such as incandescent lights, fluorescent lights, phosphorescent or luminescent lights, a laser, light-emitting diode, etc., including arrays thereof. The light source preferably includes a pattern-forming element operatively associated with a controller, as noted above. In some embodiments, the light source or pattern forming element comprises a digital (or deformable) micromirror device (DMD) with digital light processing (DLP), a spatial modulator (SLM), or a microelectromechanical system (MEMS) mirror array, a mask (aka a reticle), a silhouette, or a combination thereof. See, U.S. Pat. No. 7,902,526. Preferably the light source comprises a spatial light modulation array such as a liquid crystal light valve array or micromirror array or DMD (e.g., with an operatively associated digital light processor, typically in turn under the control of a suitable controller), configured to carry out exposure or irradiation of the polymerizable liquid without a mask, e.g., by maskless photolithography. See, e.g., U.S. Pat. Nos. 6,312,134; 6,248,509; 6,238,852; and 5,691,541.

Figure 4:
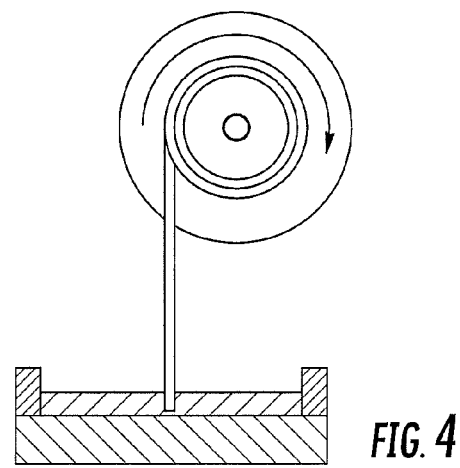
FIG. 4 illustrates various alternate carriers for use in the present invention.

Alternate carriers and actuator/drive arrangements are shown in FIG. 4. Numerous variations can be employed, including a take-up reel, an XYZ drive assembly (e.g., as commonly used on an automated microscope stage), etc. In the embodiment illustrated in FIG. 2 the drive assembly will generally comprise a worm gear and motor, a rack and pinion and motor, a hydraulic, pneumatic, or piezoelectric drive, or the like, adapted to move or advance the carrier away from the build surface in the vertical or "Z" direction only. In the alternative embodiment shown in FIG. 4 a spool or take-up reel can be utilized, with associated drives or actuators and guides (not shown), particularly when the product being fabricated is an elongated rod or fiber (discussed further below). In an alternate embodiment, a pair of take-up reels with associated guides, and associated drives or actuators (not shown), can be mounted on the linear stage to provide movement in either the X and/or Y direction in addition to or in combination with, movement in the Z direction provided by linear stage 19. In still other embodiments, an XYZ drive assembly like that used in an automated microscope can be used in place of linear stage 19 to move or advance the carrier away from the build surface in the X, Y, and/or Z direction, e.g., at an angle, or at changing angles, or combinations of directions at various stages. Thus advancement away from the build plate can be carried out solely in the Z (or vertical) direction, or in at least the Z direction, by combining movement in the Z direction with movement in the X and/or Y directions. In some embodiments, there may be movement in the X and/or Y directions concurrently with movement in the Z direction, with the movement in the X and/or Y direction hence occurring during polymerization of the polymerizable liquid (this is in contrast to the movement described in Y. Chen et al., or M. Joyce, supra, which is movement between prior and subsequent polymerization steps for the purpose of replenishing polymerizable liquid). In the present invention such movement may be carried out for purposes such as reducing "burn in" or fouling in a particular zone of the build surface.

Because an advantage of some embodiments of the present invention is that the size of the build surface on the semipermeable member (i.e., the build plate or window) may be reduced due to the absence of a requirement for extensive lateral "throw" as in the Joyce or Chen devices noted above, in the methods, systems and apparatus of the present invention lateral movement (including movement in the X and/or Y direction or combination thereof) of the carrier and object (if such lateral movement is present) is preferably not more than, or less than, 80, 70, 60, 50, 40, 30, 20, or even 10 percent of the width (in the direction of that lateral movement) of the build region.

While in some embodiments the carrier is mounted on an elevator to advance up and away from a stationary build plate, on other embodiments the converse arrangement may be used: That is, the carrier may be fixed and the build plate lowered to thereby advance the carrier away therefrom. Numerous different mechanical configurations will be apparent to those skilled in the art to achieve the same result, in all of which the build plate is "stationary" in the sense that no lateral (X or Y) movement is required to replenish the inhibitor thereon, or no elastic build plate that must be stretched and then rebound (with associated over-advance, and back-up of, the carrier) need be employed.

Depending on the choice of material from which the carrier is fabricated, and the choice of polymer or resin from which the article is made, adhesion of the article to the carrier may sometimes be insufficient to retain the article on the carrier through to completion of the finished article or "build." For example, an aluminum carrier may have lower adhesion than a poly(vinyl chloride) (or "PVC") carrier. Hence one solution is to employ a carrier comprising a PVC on the surface to which the article being fabricated is polymerized. If this promotes too great an adhesion to conveniently separate the finished part from the carrier, then any of a variety of techniques can be used to further secure the article to a less adhesive carrier, including but not limited to the application of adhesive tape such as "Greener Masking Tape for Basic Painting #2025 High adhesion" to further secure the article to the carrier during fabrication.

Soluble sacrificial layers. In some embodiments, a soluble sacrificial layer or release layer may be established between the carrier and the three-dimensional object, so that that sacrificial layer may be subsequently solubilized to conveniently release the three-dimensional object from the carrier once fabrication is complete. Any suitable sacrificial layer, such as an adhesive, that may be coated or otherwise provided on the carrier may be employed, and any suitable solvent (e.g., polar and non-polar organic solvents, aqueous solvents, etc. to solubilize the sacrificial release layer may be employed, though the sacrificial layer and its corresponding solvent should be chosen so that the particular material from which the three-dimensional object is formed is not itself unduly attacked or solubilized by that solvent. The sacrificial layer may be applied to the carrier by any suitable technique, such as spraying, dip coating, painting, etc. Examples of suitable materials for the soluble sacrificial release layer (and non-limiting examples of corresponding solvents) include but are not limited to: cyanoacrylate adhesive (acetone solvent); poly(vinylpyrrolidone) (water and/or isopropyl alcohol solvent); lacquers (acetone solvent); polyvinyl alcohol, polyacrylic acid, poly(methacrylic acid), polyacrylamide, polyalkylene oxides such as poly(ethylene oxide), sugars and saccharides such as sucrose and dextran (all water or aqueous solvents); etc. Lower surface energy solvents are in some embodiments particularly preferred.

In some embodiments of the invention, the actuator/drive and/or associated controller are configured to only advance the carrier away from the build plate (e.g., is unidirectional), as discussed further below.

In some embodiments of the invention, the actuator/drive and/or associated controller are configured as a continuous drive (as opposed to a step-wise drive), as also discussed below.

3. Methods.

As noted above, the present invention provides a method of forming a three-dimensional object, comprising the steps of: (a) providing a carrier and a build plate, said build plate comprising a semipermeable member, said semipermeable member comprising a build surface and a feed surface separate from said build surface, with said build surface and said carrier defining a build region therebetween, and with said feed surface in fluid contact with a polymerization inhibitor; then (concurrently and/or sequentially) (b) filling said build region with a polymerizable liquid, said polymerizable liquid contacting said build segment, (c) irradiating said build region through said build plate to produce a solid polymerized region in said build region, with a liquid film release layer comprised of said polymerizable liquid formed between said solid polymerized region and said build surface, the polymerization of which liquid film is inhibited by said polymerization inhibitor; and (d) advancing said carrier with said polymerized region adhered thereto away from said build surface on said stationary build plate to create a subsequent build region between said polymerized region and said top zone. In general the method includes (e) continuing and/or repeating steps (b) through (d) to produce a subsequent polymerized region adhered to a previous polymerized region until the continued or repeated deposition of polymerized regions adhered to one another forms said three-dimensional object.

Since no mechanical release of a release layer is required, or no mechanical movement of a build surface to replenish oxygen is required, the method can be carried out in a continuous fashion, though it will be appreciated that the individual steps noted above may be carried out sequentially, concurrently, or a combination thereof. Indeed, the rate of steps can be varied over time depending upon factors such as the density and/or complexity of the region under fabrication.

Also, since mechanical release from a window or from a release layer generally requires that the carrier be advanced a greater distance from the build plate than desired for the next irradiation step, which enables the window to be recoated, and then return of the carrier back closer to the build plate (e.g., a "two steps forward one step back" operation), the present invention in some embodiments permits elimination of this "back-up" step and allows the carrier to be advanced unidirectionally, or in a single direction, without intervening movement of the window for re-coating, or "snapping" of a pre-formed elastic release-layer.

In some embodiments, the advancing step is carried out sequentially in uniform increments (e.g., of from 0.1 or 1 microns, up to 10 or 100 microns, or more) for each step or increment. In some embodiments, the advancing step is carried out sequentially in variable increments (e.g., each increment ranging from 0.1 or 1 microns, up to 10 or 100 microns, or more) for each step or increment. The size of the increment, along with the rate of advancing, will depend in part upon factors such as temperature, pressure, structure of the article being produced (e.g., size, density, complexity, configuration, etc.)

In other embodiments of the invention, the advancing step is carried out continuously, at a uniform or variable rate.

In some embodiments, the rate of advance (whether carried out sequentially or continuously) is from about 0.1 1, or 10 microns per second, up to about to 100, 1,000, or 10,000 microns per second, again depending again depending on factors such as temperature, pressure, structure of the article being produced, intensity of radiation, etc As described further below, in some embodiments the filling step is carried out by forcing said polymerizable liquid into said build region under pressure. In such a case, the advancing step or steps may be carried out at a rate or cumulative or average rate of at least 0.1, 1, 10, 50, 100, 500 or 1000 microns per second, or more. In general, the pressure may be whatever is sufficient to increase the rate of said advancing step(s) at least 2, 4, 6, 8 or 10 times as compared to the maximum rate of repetition of said advancing steps in the absence of said pressure. Where the pressure is provided by enclosing an apparatus such as described above in a pressure vessel and carrying the process out in a pressurized atmosphere (e.g., of air, air enriched with oxygen, a blend of gasses, pure oxygen, etc.) a pressure of 10, 20, 30 or 40 pounds per square inch (PSI) up to, 200, 300, 400 or 500 PSI or more, may be used. For fabrication of large irregular objects higher pressures may be less preferred as compared to slower fabrication times due to the cost of a large high pressure vessel. In such an embodiment, both the feed surface and the polymerizable liquid can be in fluid contact with the same compressed gas (e.g., one comprising from 20 to 95 percent by volume of oxygen, the oxygen serving as the polymerization inhibitor.

On the other hand, when smaller items are fabricated, or a rod or fiber is fabricated that can be removed or exited from the pressure vessel as it is produced through a port or orifice therein, then the size of the pressure vessel can be kept smaller relative to the size of the product being fabricated and higher pressures can (if desired) be more readily utilized.

As noted above, the irradiating step is in some embodiments carried out with patterned irradiation. The patterned irradiation may be a fixed pattern or may be a variable pattern created by a pattern generator (e.g., a DLP) as discussed above, depending upon the particular item being fabricated.

When the patterned irradiation is a variable pattern rather than a pattern that is held constant over time, then each irradiating step may be any suitable time or duration depending on factors such as the intensity of the irradiation, the presence or absence of dyes in the polymerizable material, the rate of growth, etc. Thus in some embodiments each irradiating step can be from 0.001, 0.01, 0.1, 1 or 10 microseconds, up to 1, 10, or 100 minutes, or more, in duration. The interval between each irradiating step is in some embodiments preferably as brief as possible, e.g., from 0.001, 0.01, 0.1, or 1 microseconds up to 0.1, 1, or 10 seconds.

In some embodiments the build surface is flat; in other the build surface is irregular such as convexly or concavely curved, or has walls or trenches formed therein. In either case the build surface may be smooth or textured.

Curved and/or irregular build plates or build surfaces can be used in fiber or rod formation, to provide different materials to a single object being fabricated (that is, different polymerizable liquids to the same build surface through channels or trenches formed in the build surface, each associated with a separate liquid supply, etc.

Carrier feed channels for polymerizable liquid. While polymerizable liquid may be provided directly to the build plate from a liquid conduit and reservoir system, in some embodiments the carrier include one or more feed channels therein. The carrier feed channels are in fluid communication with the polymerizable liquid supply, for example a reservoir and associated pump. Different carrier feed channels may be in fluid communication with the same supply and operate simultaneously with one another, or different carrier feed channels may be separately controllable from one another (for example, through the provision of a pump and/or valve for each). Separately controllable feed channels may be in fluid communication with a reservoir containing the same polymerizable liquid, or may be in fluid communication with a reservoir containing different polymerizable liquids. Through the use of valve assemblies, different polymerizable liquids may in some embodiments be alternately fed through the same feed channel, if desired.

4. Controller and Process Control.

The methods and apparatus of the invention can include process steps and apparatus features to implement process control, including feedback and feed-forward control, to, for example, enhance the speed and/or reliability of the method.

A controller for use in carrying out the present invention may be implemented as hardware circuitry, software, or a combination thereof. In one embodiment, the controller is a general purpose computer that runs software, operatively associated with monitors, drives, pumps, and other components through suitable interface hardware and/or software. Suitable software for the control of a three-dimensional printing or fabrication method and apparatus as described herein includes, but is not limited to, the ReplicatorG open source 3d printing program, 3DPrint™ controller software from 3D systems, Slic3r, Skeinforge, KISSlicer, Repetier-Host, PrintRun, Cura, etc., including combinations thereof.

Process parameters to directly or indirectly monitor, continuously or intermittently, during the process (e.g., during one, some or all of said filling, irradiating and advancing steps) include, but are not limited to, irradiation intensity, temperature of carrier, polymerizable liquid in the build zone, temperature of growing product, temperature of build plate, pressure, speed of advance, pressure, force (e.g., exerted on the build plate through the carrier and product being fabricated), strain (e.g., exerted on the carrier by the growing product being fabricated), thickness of release layer, etc.

Known parameters that may be used in feedback and/or feed-forward control systems include, but are not limited to, expected consumption of polymerizable liquid (e.g., from the known geometry or volume of the article being fabricated), degradation temperature of the polymer being formed from the polymerizable liquid, etc.

Process conditions to directly or indirectly control, continuously or step-wise, in response to a monitored parameter, and/or known parameters (e.g., during any or all of the process steps noted above), include, but are not limited to, rate of supply of polymerizable liquid, temperature, pressure, rate or speed of advance of carrier, intensity of irradiation, duration of irradiation (e.g. for each "slice"), etc.

For example, the temperature of the polymerizable liquid in the build zone, or the temperature of the build plate, can be monitored, directly or indirectly with an appropriate thermocouple, non-contact temperature sensor (e.g., an infrared temperature sensor), or other suitable temperature sensor, to determine whether the temperature exceeds the degradation temperature of the polymerized product. If so, a process parameter may be adjusted through a controller to reduce the temperature in the build zone and/or of the build plate. Suitable process parameters for such adjustment may include: decreasing temperature with a cooler, decreasing the rate of advance of the carrier, decreasing intensity of the irradiation, decreasing duration of radiation exposure, etc.

In addition, the intensity of the irradiation source (e.g., an ultraviolet light source such as a mercury lamp) may be monitored with a photodetector to detect a decrease of intensity from the irradiation source (e.g., through routine degradation thereof during use). If detected, a process parameter may be adjusted through a controller to accommodate the loss of intensity. Suitable process parameters for such adjustment may include: increasing temperature with a heater, decreasing the rate of advance of the carrier, increasing power to the light source, etc.

As another example, control of temperature and/or pressure to enhance fabrication time may be achieved with heaters and coolers (individually, or in combination with one another and separately responsive to a controller), and/or with a pressure supply (e.g., pump, pressure vessel, valves and combinations thereof) and/or a pressure release mechanism such as a controllable valve (individually, or in combination with one another and separately responsive to a controller).

In some embodiments the controller is configured to maintain the gradient of polymerization zone described herein (see, e.g., FIG. 1) throughout the fabrication of some or all of the final product. The specific configuration (e.g., times, rate or speed of advancing, radiation intensity, temperature, etc.) will depend upon factors such as the nature of the specific polymerizable liquid and the product being created. Configuration to maintain the gradient of polymerization zone may be carried out empirically, by entering a set of process parameters or instructions previously determined, or determined through a series of test runs or "trial and error"; configuration may be provided through pre-determined instructions; configuration may be achieved by suitable monitoring and feedback (as discussed above), combinations thereof, or in any other suitable manner.

5. Fabrication Products.

Three-dimensional products produced by the methods and processes of the present invention may be final, finished or substantially finished products, or may be intermediate products subject to further manufacturing steps such as surface treatment, laser cutting, electric discharge machining, etc. Intermediate products include products for which further additive manufacturing, in the same or a different apparatus, may be carried out). For example, a fault or cleavage line may be introduced deliberately into an ongoing "build" by disrupting, and then reinstating, the gradient of polymerization zone, to terminate one region of the finished product, or simply because a particular region of the finished product or "build" is less fragile than others.

Numerous different products can be made by the methods and apparatus of the present invention, including both large-scale models or prototypes, small custom products, miniature or microminiature products or devices, etc. Examples include, but are not limited to, medical devices and implantable medical devices such as stents, drug delivery depots, functional structures, microneedle arrays, fibers and rods such as waveguides, micromechanical devices, microfluidic devices, etc.

Thus in some embodiments the product can have a height of from 0.1 or 1 millimeters up to 10 or 100 millimeters, or more, and/or a maximum width of from 0.1 or 1 millimeters up to 10 or 100 millimeters, or more. In other embodiments, the product can have a height of from 10 or 100 nanometers up to 10 or 100 microns, or more, and/or a maximum width of from 10 or 100 nanometers up to 10 or 100 microns, or more. These are examples only:

Maximum size and width depends on the architecture of the particular device and the resolution of the light source and can be adjusted depending upon the particular goal of the embodiment or article being fabricated.

In some embodiments, the ratio of height to width of the product is at least 2:1, 10:1, 50:1, or 100:1, or more, or a width to height ratio of 1:1, 10:1, 50:1, or 100:1, or more.

In some embodiments, the product has at least one, or a plurality of, pores or channels formed therein, as discussed further below.

The processes described herein can produce products with a variety of different properties. Hence in some embodiments the products are rigid; in other embodiments the products are flexible or resilient. In some embodiments, the products are a solid; in other embodiments, the products are a gel such as a hydrogel. In some embodiments, the products have a shape memory (that is, return substantially to a previous shape after being deformed, so long as they are not deformed to the point of structural failure). In some embodiments, the products are unitary (that is, formed of a single polymerizable liquid); in some embodiments, the products are composites (that is, formed of two or more different polymerizable liquids). Particular properties will be determined by factors such as the choice of polymerizable liquid(s) employed.

In some embodiments, the product or article made has at least one overhanging feature (or "overhang"), such as a bridging element between two supporting bodies, or a cantilevered element projecting from one substantially vertical support body. Because of the unidirectional, continuous nature of some embodiments of the present processes, the problem of fault or cleavage lines that form between layers when each layer is polymerized to substantial completion and a substantial time interval occurs before the next pattern is exposed, is substantially reduced. Hence, in some embodiments the methods are particularly advantageous in reducing, or eliminating, the number of support structures for such overhangs that are fabricated concurrently with the article.

The present invention is explained in greater detail in the following non-limiting Examples.

EXAMPLE 1

Inhibitor Transfer to Build Surface from a Separate Feed Surface

Figure 5A:
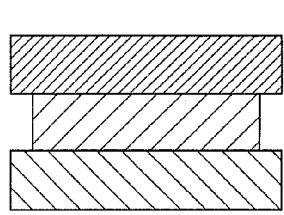
FIG. 5A schematically illustrates a polymerization inhibitor in a rigid build plate aiding to establish a non-polymerized film on the surface thereof.
Figure 5C:
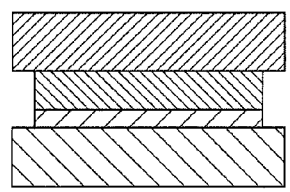
FIG. 5C illustrates the embodiment of FIGS. 5A-5B, after separation of the two plates.
Figure 5C:
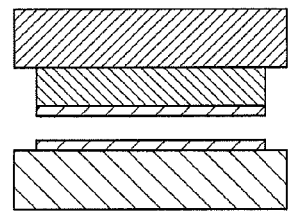

A drop of ultraviolet (UV) curable adhesive was placed on a metal plate and covered with 10 mm thick plate of TEFLON® AF fluoropolymer (a amorphous, glassy polymer) as shown in FIG. 5a. UV radiation was supplied to the adhesive from the side of Teflon AF as shown in FIG. 5b. After UV exposure the two plates were separated. It was found that no force was required to separate the two plates. Upon examination of the samples it was discovered that the adhesive was cured only next to the metal plate, and that a thin film of uncured adhesive was present on the Teflon AF fluoropolymer plate and also on the cured portion of the adhesive as shown in FIG. 5c.

Figure 5D:
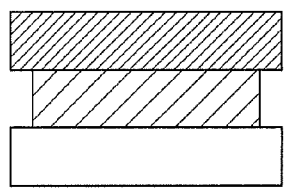
FIG. 5D illustrates an experiment similar to FIGS. 5A to 5C, except that clean glass is employed.
Figure 5F:
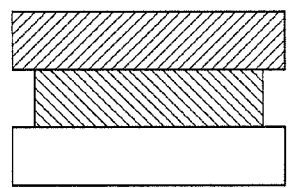
FIG. 5F illustrates the embodiment of FIGS. 5D to 5E, after separation of the two plates.
Figure 5F:
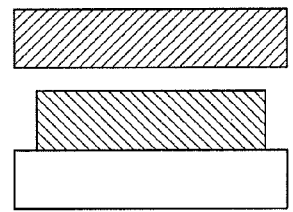
Figure 5G:
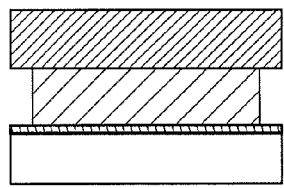
FIG. 5G illustrates an experiment similar to FIGS. 5A to 5C, and FIGS. 5D to 54, except that glas treated with a release layer was used.
Figure 5I:
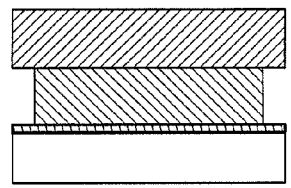
FIG. 5I illustrates the embodiment of FIGS. 5G to 5H, after separation of the two plates.
Figure 5I:
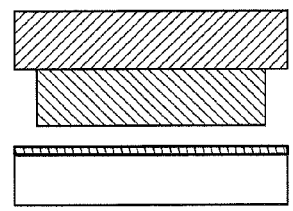

Two controlled experiments were also performed where clean glass (FIGS. 5d-5f) and also glass treated with release layer (FIGS. 5g-5i) was used. It was confirmed that considerable force was needed to separate clean glass from the metal and it was found that adhesive remained on the glass. Less force was needed to separate the treated glass, while adhesive remained on the metal plate.

The chemical phenomenon which describes the observed behavior is oxygen inhibition of the radical polymerization reaction. In particular, Teflon AF has a very high oxygen permeability coefficient. Constant supply of oxygen through 10 mm think Teflon AF is sufficient to prevent a thin layer of acrylate adhesive from polymerization. The thickness of uncured adhesive layer in the above experiment was on the order of 10 microns and it can be increased or decreased by varying the amount of photo initiator present in the adhesive.

EXAMPLE 2

Inhibitor Transfer through Build Plate to Build Surface

Figure 6A:
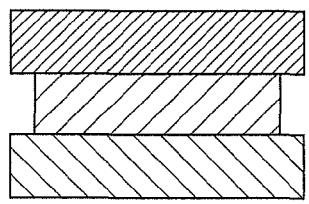
FIG. 6A schematically illustrates a structure for showing the migration of an inhibitor (in this case oxygen) through a build plate from a feed surface on the back of the plate to a build surface on the front of a plate to aid in establishing a non-polymerized film on the build surface.
Figure 6B:
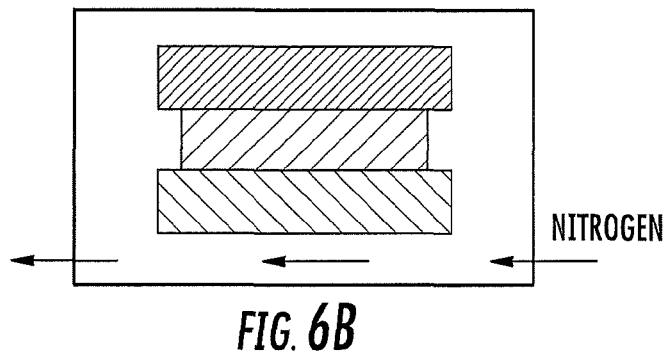
FIG. 6B shows the structure of a pair of samples of FIG. 6A being exposed to a nitrogen environment.
Figure 6D:
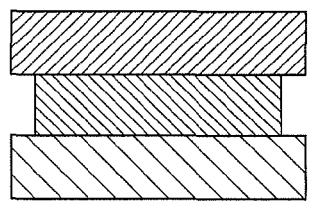
FIG. 6D shows separation of the structure of FIG. 6C, with the adhesive completely cured.
Figure 6D:
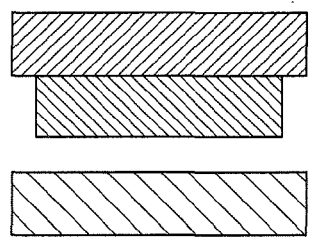
Figure 6F:
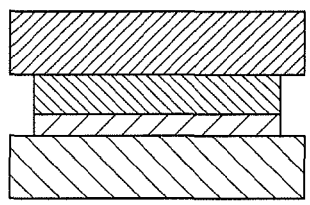
FIG. 6F shows separation of the structure of FIG. 6F, with the adhesive only cured adjacent the metal plate.
Figure 6F:
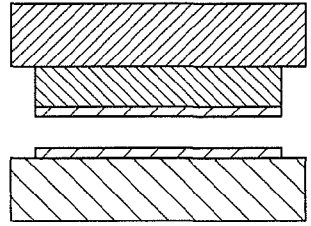

Samples 1 and 2 were prepared in a similar manner wherein a drop of UV curable adhesive was placed on a metal plate and covered with 10 mm thick plate of TEFLON® AF fluoropolymer as shown in FIG. 6a. Both samples were exposed to a nitrogen environment to eliminate any presence of oxygen as shown in FIG. 6b. Next both samples were brought into a standard atmosphere environment and Sample 1 was immediately exposed to UV radiation while Sample 2 was exposed to UV radiation 10 minutes after being in the atmosphere environment. Both samples were exposed to the same amount of UV radiation as shown in FIG. 6C and FIG. 6E. Upon examination of the samples after UV exposure it was discovered that the adhesive was cured completely in Sample 1 as shown in FIG. 6D and only next to the metal plate in Sample 2 as shown in FIG. 6F. A thin film of uncured adhesive was present on the Teflon AF fluoropolymer plate and also on the cured portion of the adhesive for Sample 2. This experiment shows that the inhibitor, oxygen, was transferred through Teflon AF plate to the adhesive during the 10 minute period of being exposed to the atmosphere environment.

EXAMPLE 3

Increasing Fabrication Rate: Pressure

A highly oxygen permeable, and UV transparent material is used as the bottom of a chamber filled with photocurable resin in a device of the invention. During construction, the top of an object is attached to a support plate which is moved up at a substantially constant speed while the bottom portion of the object is constantly being formed just above the bottom of the chamber. The gap between the bottom of the object and the bottom of the chamber is always filled with resin. As the object is being formed and advanced, the resin in the gap is constantly replenished with supply resin contained in the chamber.

Figure 7:
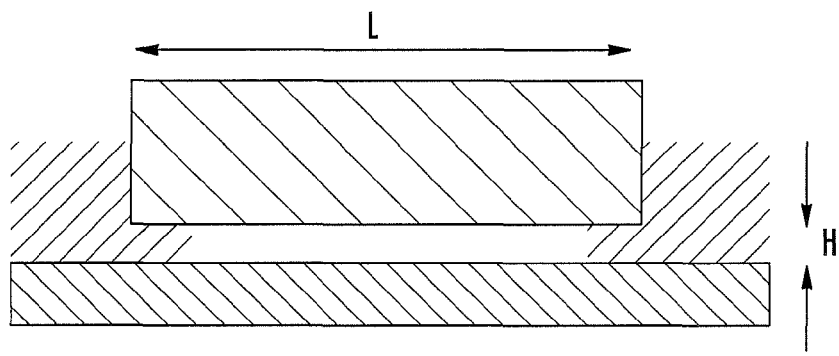
FIG. 7 schematically illustrates a growing three-dimensional object being advanced away from a build surface, and the gap that must be filled therebetween before subsequent polymerization can be carried out.

The speed of the object's formation depends on the viscosity of the resin η, atmospheric pressure P, the height of the gap between the object and the bottom of the chamber h, and the linear dimension L of the object's bottom surface. Simple calculations are performed to estimate this speed using the theory of viscous flow between two parallel plates. The time τ which is required to fill the gap shown on FIG. 7 is given by the equation:

$$\tau \sim \left(\frac{L}{h}\right)^2 \frac{\eta}{P}$$

Assuming:
L~100 mm
h~100 microns
η~100 cPoise
P~1 atm

Figure 8:
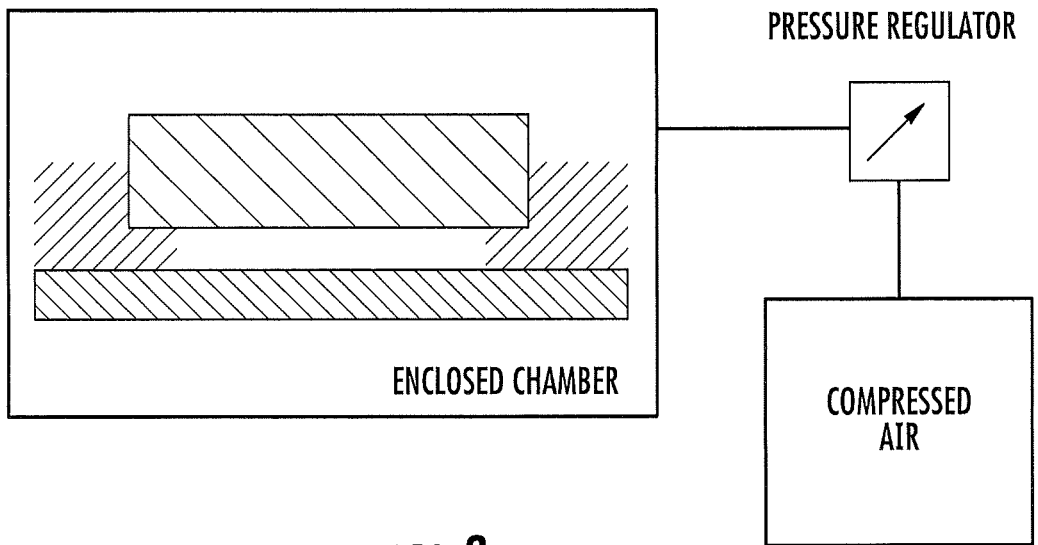
FIG. 8 schematically illustrates an embodiment of the invention which provides for the application of pressure to speed the filling of the gap shown in FIG. 8.

In this illustrative embodiment, the time τ is estimated to be of an order of 1 second, resulting in fabrication speeds of 100 microns per second or 5 minutes per inch. These calculations assume that the thickness of the uncured resin is maintained at about 100 microns. Depending on the chemistry of the resin and permeability of the base plate, this parameter may vary. If, for example, the gap is 25 microns, then fabrication speeds at atmospheric pressure will decrease according to Equation 1 by a factor of 16. However, increasing the ambient pressure to greater than atmospheric pressure, e.g., by applying external pressure on the order of 150 PSI as shown in FIG. 8, may in some embodiments increase fabrication speed by a factor of 10.

When oxygen is the polymerization inhibitor, the gap of uncured resin can be controlled by altering the physical environment in the enclosed chamber contacting feed surface. For example, an atmosphere of pure oxygen, or enriched in oxygen (e.g., 95% oxygen 5% carbon dioxide) can be provided in place of compressed air, in order to increase the gap resulting in an increase of fabrication time.

EXAMPLE 4

Fabrication of Rods and Fibers

Figure 9:
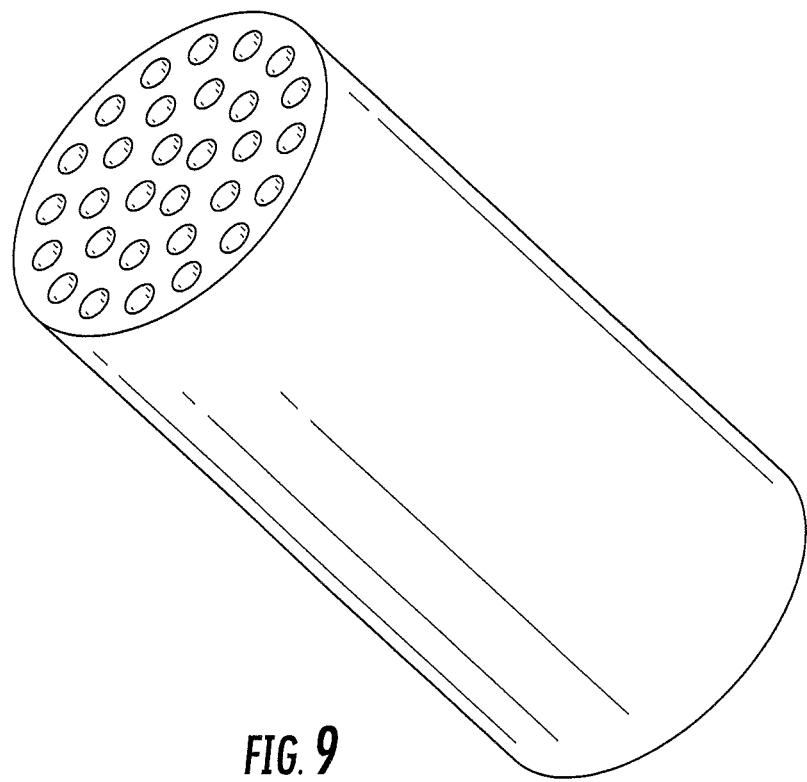
FIG. 9 illustrates a rod or fiber that can be produced by the methods and apparatus of the present invention.

The methods of the present invention can be used to make an elongate rod or fiber as shown in FIG. 9, the rod or fiber having (for example) a width or diameter of 0.01 or 0.1 to 10 or 100 millimeters. While a circular cross-section is shown, any suitable cross-section can be utilized, including elliptical, polygonal (triangular, square, pentagonal, hexagonal, etc.) irregular, and combinations thereof. The rod or fiber can have a plurality of elongated pores or channels formed therein (e.g., 1, 10, 100 1,000, 10,000 or 100,000 or more) of any suitable diameter (e.g., 0.1 or 1 microns, up to 10 or 100 microns or more) and any suitable cross-section as described above. Unpolymerized liquid in the pores or channels can be removed (if desired) by any suitable technique, such as blowing, pressure, vacuum, heating, drying and combinations thereof. The length of the rod or fiber can be increased by utilizing a take-up reel as described above, and the speed of fabrication of the rod or fiber can be increased by carrying out the polymerization under pressure as described above. A plurality of such rods or fibers can be constructed concurrently from a single build plate by providing a plurality of independent carriers or take-up reels. Such rods or fibers can be used for any purpose, such as utilizing each pore or channel therein as an independent channel in a microfluidic system.

EXAMPLE 5

Illustrative Apparatus

An apparatus that can be used to carry out the present invention was assembled as described above, with a LOCTITE™ UV Curing Wand System as the ultraviolet light source, a build plate comprised of 0.0025 inch thick Teflon AF 2400 film from Biogeneral clamped in a window and tensioned to substantial rigidity with a tensioning ring, optical components: from Newport Corporation, Edmund Optics, and Thorlabs, a DLP LightCrafter Development Kit from Texas Instruments as the digital projector, a THK Co., LTD ball screw linear stage serving as an elevator for the carrier, a continuous servo from Parallax Inc as the elevator and carrier drive or motor, a motion controller based on a Propeller microcontroller from Parallax Inc., a position controller based on a magnetic encoder from Austria Microsystems, motion control software written in SPIN language created by Parallax, open source Slic3r 3D slicing software, and image control software written using Qt framework and Visual C++.

Various different example articles fabricated with this device by the methods described herein are described further below.

EXAMPLE 6

Fabrication of a 700 Micron Microneedle Array

Figure 10:
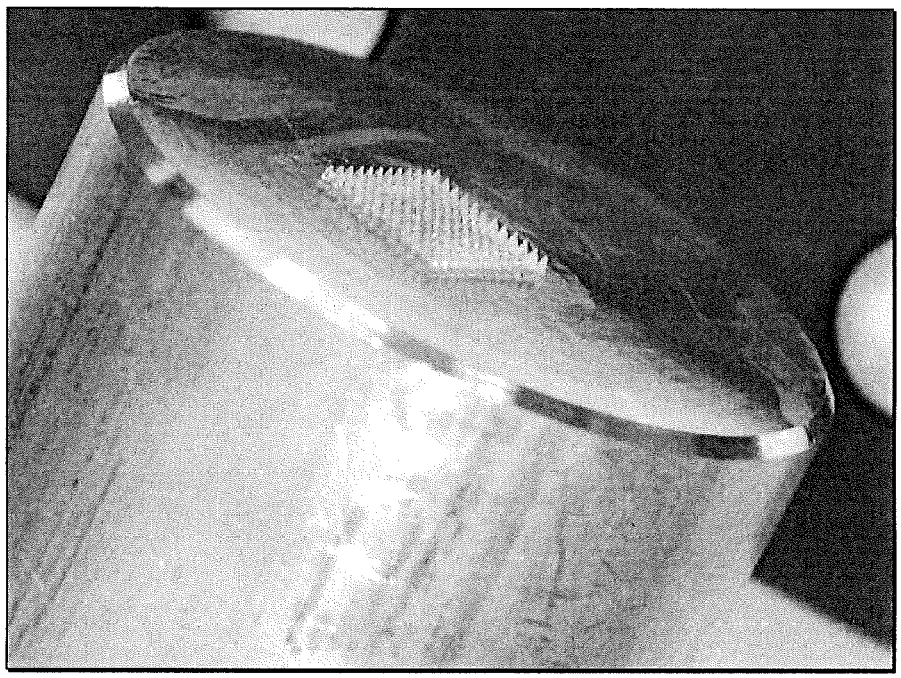
FIG. 10 is a photograph of a microneedle array fabricated with methods and apparatus of the present invention. The diameter of the carrier on which the array is held is approximately the same as a United States twenty-five cent coin (or "quarter"). Essentially the same carrier is used in the additional examples illustrated below.

Using an apparatus as described in the example above, trimethylolpropane triacrylate as the polymerizable liquid, and Diphenyl(2,4,6-trimethylbenzoyl)phosphine oxide as a photoinitiator, the array of microneedles shown in FIG. 10 was made. The carrier was advanced unidirectionally by the ball screw at a continuous rate of 10 microns per second and successive exposures were carried out every 2 microns along the building height at a duration of 0.2 seconds per exposure. The total number of successive exposures was 350 and the total fabrication time was 70 seconds.

EXAMPLE 7

Fabrication of a 2000 Micron Microneedle Array

Figure 11:
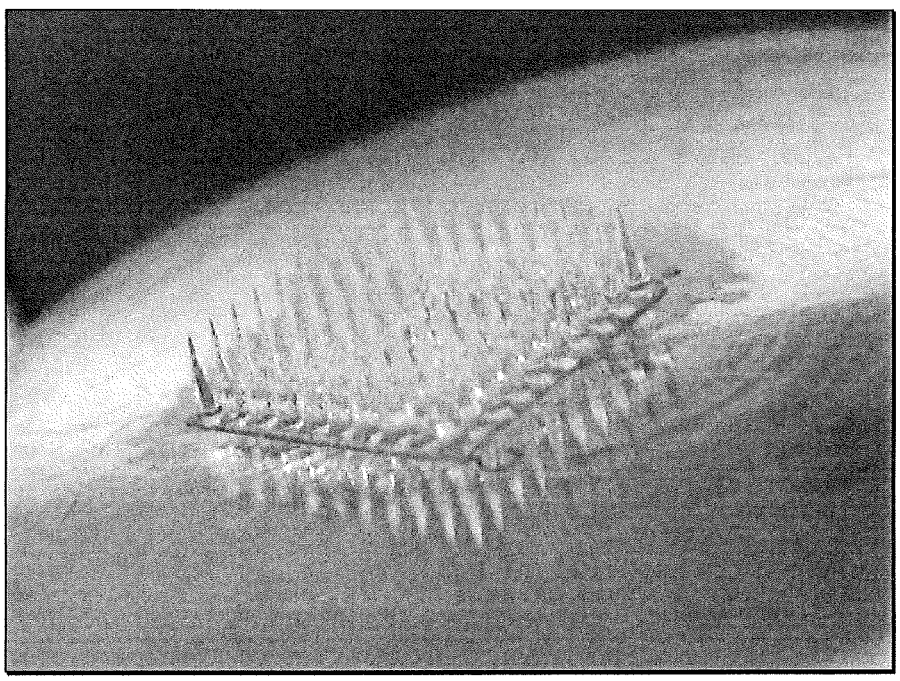
FIG. 11 is a photograph of a second microneedle array fabricated with methods and apparatus of the present invention.

The 2000 micron microneedle array shown in FIG. 11 was made in like manner as described in example 6 above, with 1000 successive exposures over a total fabrication time of 200 seconds.

It will be apparent that other arrays, for example with microneedles having widths of from 5 to 500 micrometers and heighths of 5 to 2000 micrometers or more, can be fabricated in like manner. While a square cross-section is shown, any suitable cross-section can be utilized, including circular, elliptical, polygonal (triangular, rectangular, pentagonal, hexagonal, etc.) irregular, and combinations thereof. The spacing between microneedles can be varied as desired, for example from 5 to 100 micrometers, and the microneedles or other microstructures can be arranged with respect to one another in any suitable pattern, e.g., square, rectangular, hexagonal, etc.

EXAMPLE 8

Fabrication of a Ring Structure

Figure 12:
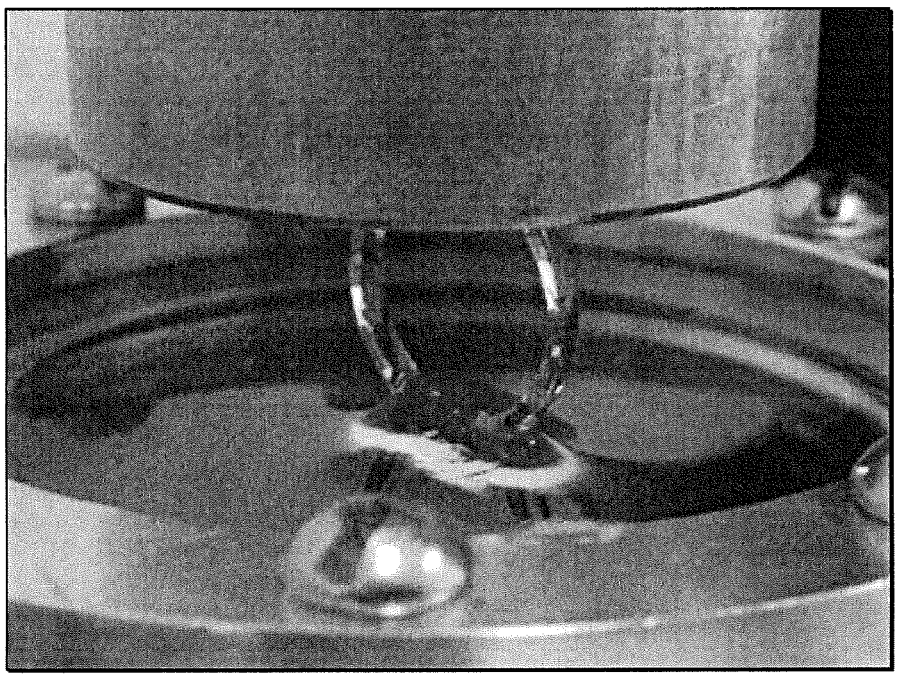
FIG. 12 is a photograph of a ring structure being fabricated with methods and apparatus of the present invention. Note the extensive "overhang" during fabrication.
Figure 13:
FIG. 13 is a photograph of the completed ring of FIG. 12.

A ring was fabricated using the apparatus described in Example 5 above, trimethylolpropane triacrylate as the polymerizable liquid, and Diphenyl(2,4,6-trimethylbenzoyl) phosphine oxide as photoinitiator. The carrier was advanced unidirectionally by the ball screw at a continuous rate of 20 microns per second and successive exposures were carried every 10 microns along the building height at a duration of 0.5 seconds per exposure. The total number of successive exposures was 1040 and the total fabrication time was 520 seconds. FIG. 12 shows the ring during fabrication, and FIG. 13 shows the ring after fabrication. Note the absence of supports for extensively overhung elements during fabrication.

EXAMPLE 9

Fabrication of a Chess Piece

Figure 14:
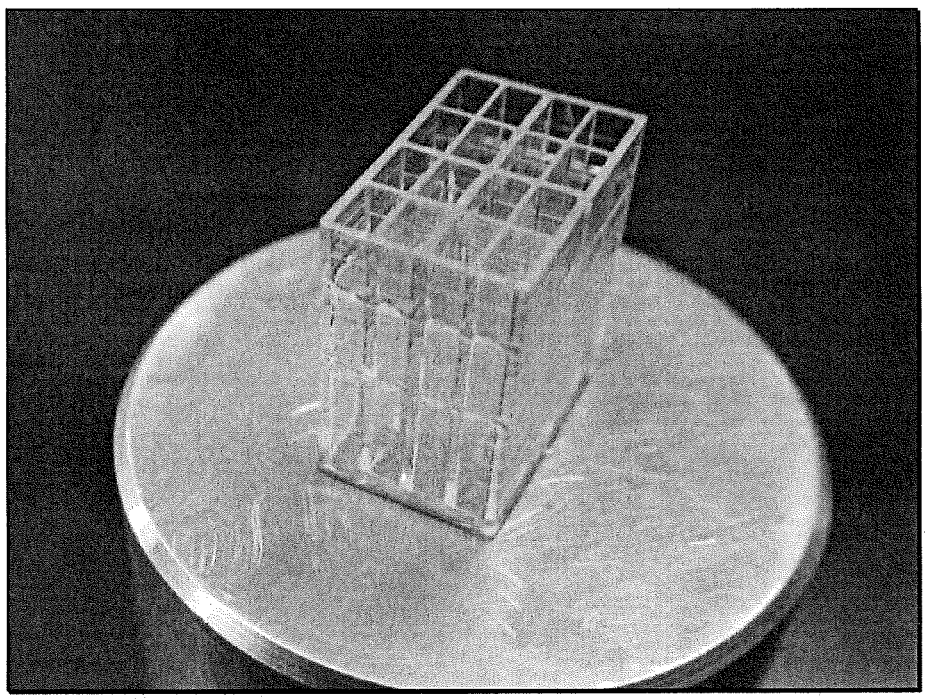
FIG. 14 is a photograph of four chess piece structures fabricated with methods and apparatus of the present invention.

The chess piece shown in FIG. 14 was made using the apparatus described in the examples above, trimethylolpropane triacrylate as the polymerizable liquid, and Diphenyl(2,4,6-trimethylbenzoyl)phosphine oxide as photoinitiator. The carrier was advanced unidirectionally by the ball screw at a continuous rate of 20 microns per second and successive exposures were carried every 10 microns along the building height at a duration of 0.5 seconds per exposure. The total number of successive exposures was 1070 and the total fabrication time was 535 seconds.

EXAMPLE 10

Fabrication of a Ribbed Rectangular Prism

Figure 15:
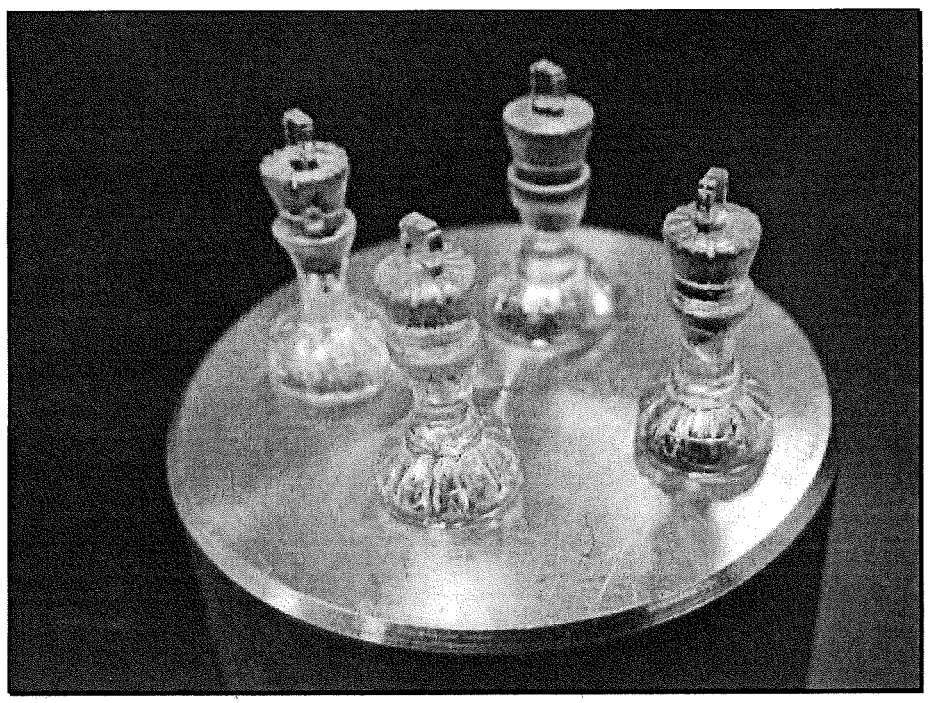
FIG. 15 is a photograph of a rectangular prism structure fabricated with methods and apparatus of the present invention.

The ribbed rectangular prism shown in FIG. 15 was made using the apparatus described in the Examples above, trimethylolpropane triacrylate as the polymerizable liquid, and Diphenyl(2,4,6-trimethylbenzoyl)phosphine oxide as the photoinitiator. The carrier was advanced unidirectionally by the worm gear at a continuous rate of 20 microns per second and successive exposures were carried every 10 microns along the building height at a duration of 0.5 second per exposure. The total number of successive exposures was 800 and the total fabrication time was 400 seconds.

EXAMPLE 11

Fabrication of a Coiled or Spiraled Structure

Figure 16:
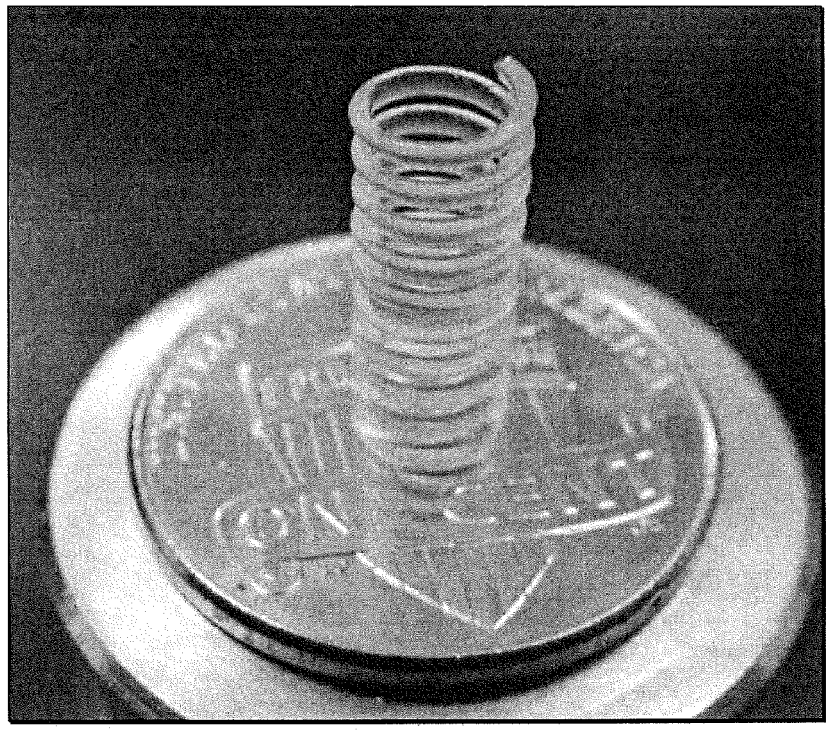
FIG. 16 is a photograph of a coil structure fabricated by methods and apparatus of the present invention. Note the extensive "overhang" during fabrication through to the completed structure.

The coil or spiral shown in FIG. 16 was made using the apparatus described in the examples above, trimethylolpropane triacrylate as the polymerizable liquid, and Diphenyl(2,4,6-trimethylbenzoyl)phosphine oxide as the photoinitiator. The carrier was advanced unidirectionally by the ball screw at a continuous rate of 20 microns per second and successive exposures were carried every 10 microns along building height at a duration of 0.5 seconds per exposure. The total number of successive exposures was 970 and the total fabrication time was 485 seconds.

Note that this extensively cantilevered structure was fabricated free of any supporting structures.

EXAMPLE 12

Curing Depth vs. Exposure Time

Figure 17:
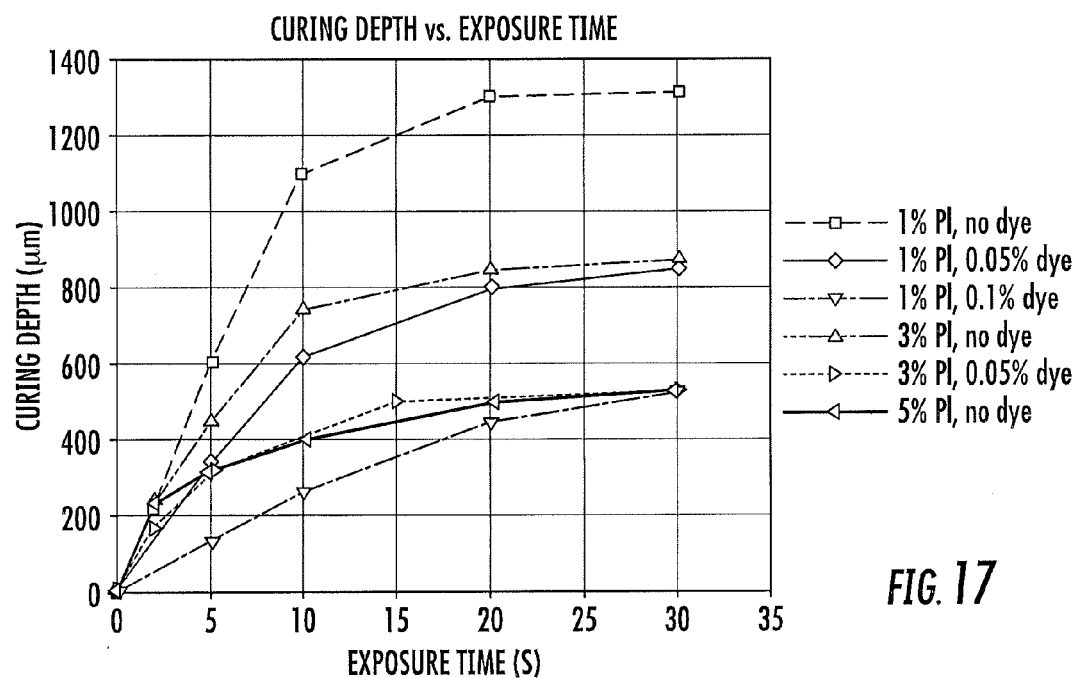
FIG. 17 illustrates the effects of dye and photoinitiator on cure time.

An experiment was performed with various concentrations of amber candle dye and photo initiator (PI) in trimethylolpropane triacrylate as the polymerizable liquid and Diphenyl (2,4,6-trimethylbenzoyl)phosphine oxide as photoinitiator. Results are shown in FIG. 17. The image used was a 6 mm circle, which produced a disk-like part in the resin bath, when cured. The thickness of the disk varied based on the exposure time and the concentration of photo initiator and dye in the resin. All resin mixtures would begin curing quickly and approach a limiting value. The optimal resin should cure in a short period of time and the limiting value should be as small as possible. The two resins that best fit those criteria are the 3% photo initiator with 0.05% dye (fine dots) and 5% photoinitiator with no dye (solid). These resins also produce the best printed parts in terms of feature contrast and clarity.

Figure 18:
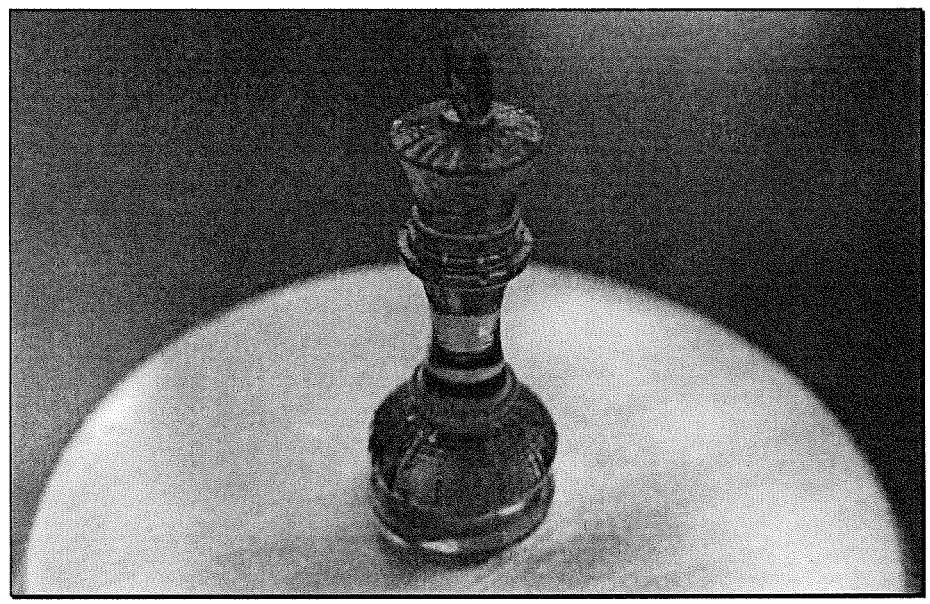
FIG. 18 is a photograph of a chess piece similar to those shown FIG. 14 above, but made with a dyed resin by the methods of the present invention.

A chess piece made with such a dye-containing resin is shown in FIG. 18.

EXAMPLE 13

Carrier Soluble Sacrificial (or Release) Layers

A deficiency of prior techniques is that the requirement to "break" adhesion from the build plate, e.g., by sliding the build plate, or by using an elastic build plate, made it problematic to employ a release layer or soluble adhesive layer on the carrier that might prematurely fail during the fabrication process. The present invention facilitates the employment of a release layer on the carrier during fabrication.

Figure 19:
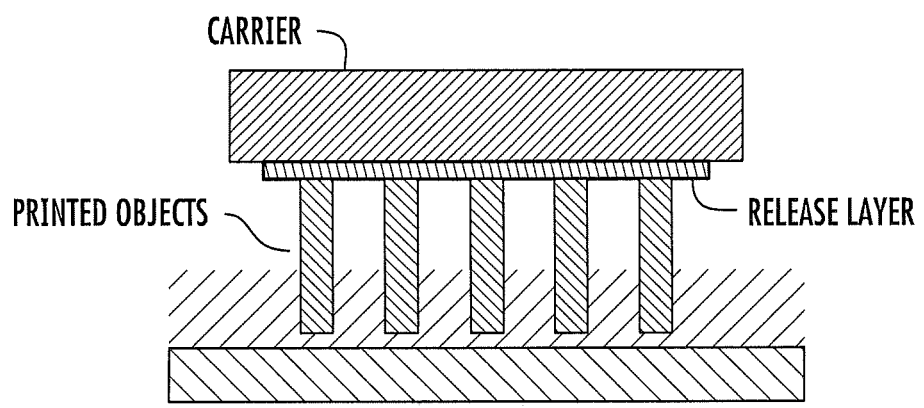
FIG. 19 schematically illustrates the fabrication of a plurality of articles on the carrier, the carrier having a release layer thereon.
Figure 20:
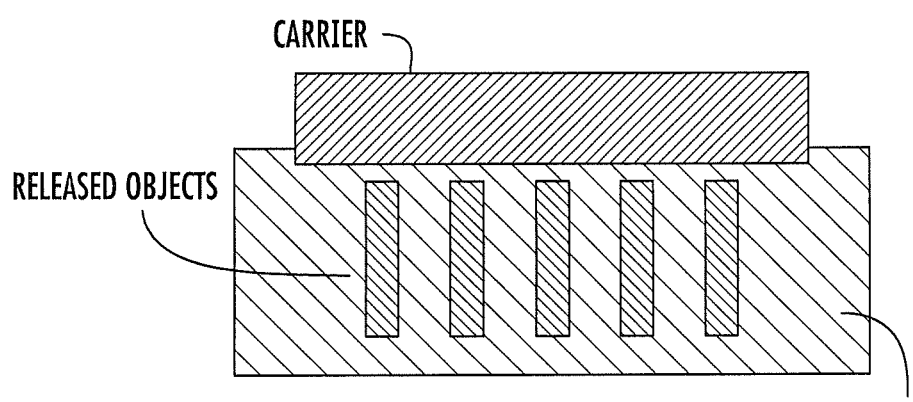
FIG. 20 schematically illustrates the release of a plurality of articles from the carrier with a release layer.

The surface of the carrier can be coated with a release layer, i.e., a soluble sacrificial layer (e.g., cyanoacrylate adhesive), and array of objects can be printed as shown in FIG. 19. Any suitable thickness of release layer can be used, for example from 100 nanometers to 1 millimeter. Submerging the carrier with the fabricated objects into an appropriate solvent (e.g., acetone for cyanoacrylate adhesive) that selectively dissolves or solubilizes the release layer then releases the objects from the carrier as shown in FIG. 20.

EXAMPLE 14

Fabricating Rectangular Prisms on a Release Layer

Figure 21:
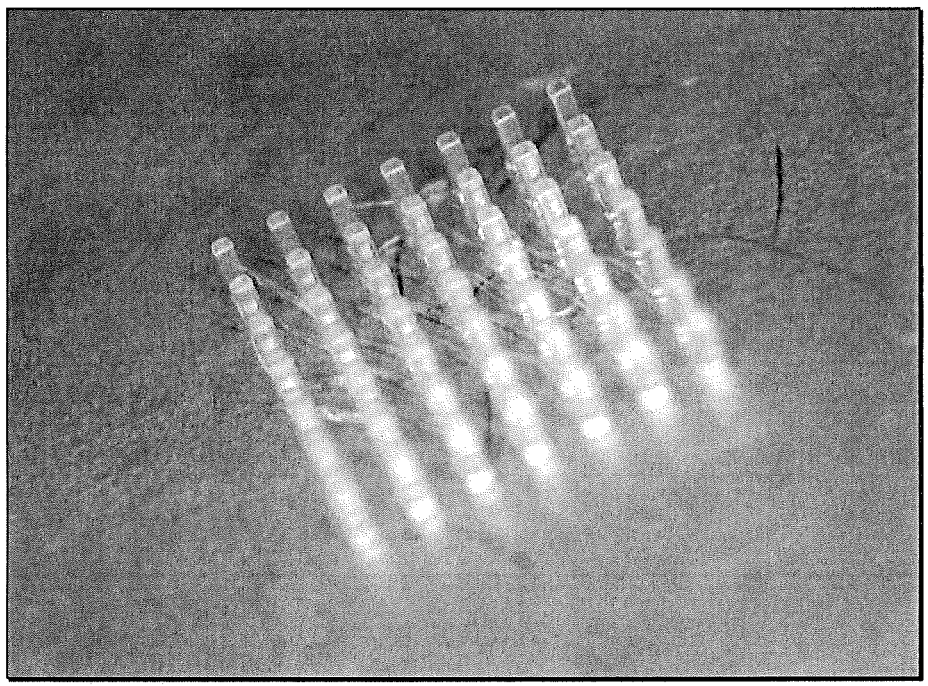
FIG. 21 is a photograph of an array of prisms fabricated by methods and apparatus of the present invention, on a release layer.
Figure 22:
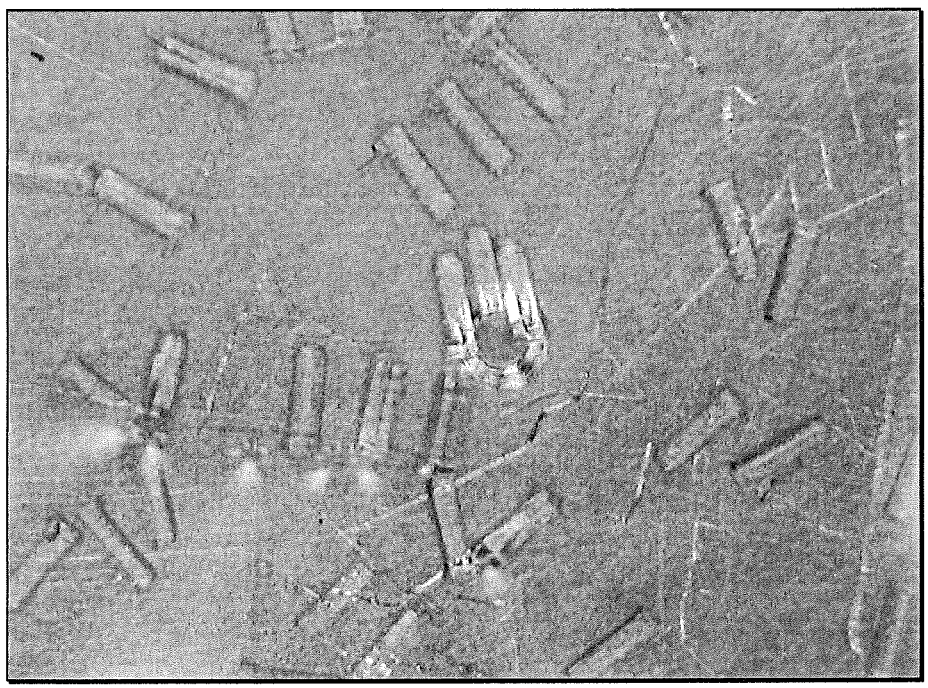
FIG. 22 is a photograph of the prisms shown in FIG. 21 after release.

The array of rectangular prisms with dimensions of 200×200×1000 micrometers shown in FIG. 21 was made using the apparatus described above, trimethylolpropane triacrylate as the polymerizable liquid, diphenyl(2,4,6-trimethylbenzoyl) phosphine oxide as the photoinitiator, and cyanoacrylate adhesive as release layer. The carrier was advanced by the ball screw at a continuous rate of 10 microns per second and successive exposures were carried every 10 microns along the building height at a duration of 1 second per exposure. The total number of successive exposures was 100 and the total fabrication time was 100 seconds. The cyanoacrylate release layer was then dissolved by acetone to produce free floating prisms as shown in FIG. 22.

EXAMPLE 15

Fabrication of Cylindrical Cage Structures

Figure 23:
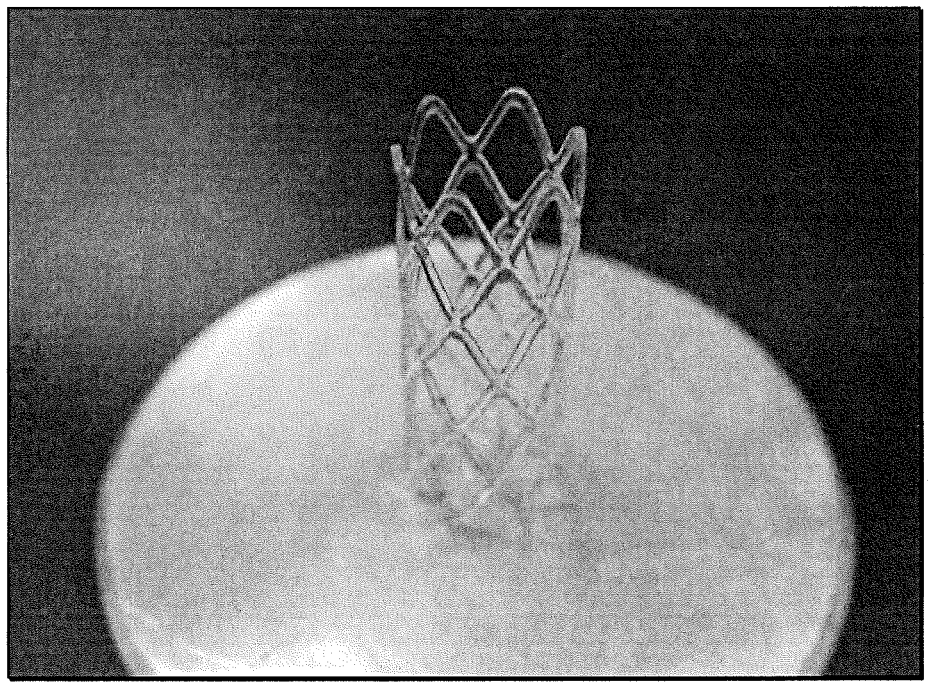
FIG. 23 is a photograph of a cylindrical caged structure produced by methods and apparatus of the present invention.

The cylindrical cage structure of FIG. 23 was made using the apparatus described in the Example above, trimethylolpropane triacrylate as the polymerizable liquid, and diphenyl (2,4,6-trimethylbenzoyl)phosphine oxide as photoinitiator. The carrier was advanced by the ball screw at a continuous rate of 20 microns per second and successive exposures were carried out every 10 micron along the building height at a duration of 0.5 seconds per exposure. The total number of successive exposures was 1400 and the total fabrication time was 700 seconds. No removable supporting structures for cantilevered features or "overhangs" were used.

EXAMPLE 16

Fabrication of Structures from a Hydrogel

Figure 24:
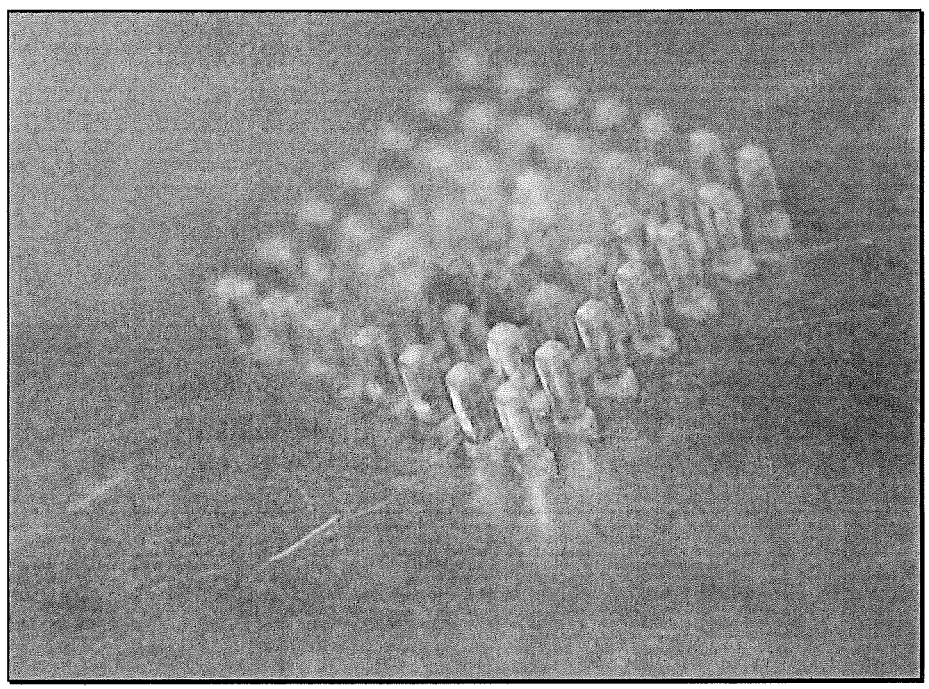
FIG. 24 is a photograph of an array similar to that of FIG. 21, and produced by essentially the same methods, except that it comprises a polyethylene glycol polymer.
Figure 25:
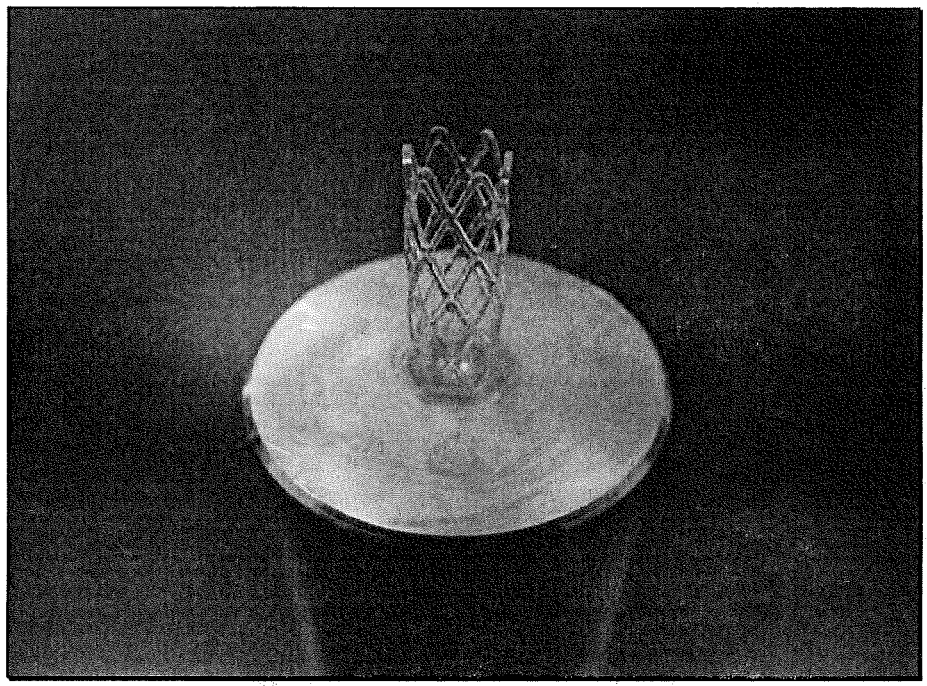
FIG. 25 is a photograph of a cylindrical cage structure similar to that of FIG. 23, and produced by substantially the same methods, except that it comprises a polyethylene glycol polymer. The part was noted to be flexible.

FIG. 24 and FIG. 25 are photographs of array structures and cage structures, respectively, produced in like manner as those described above, except that they were fabricated using PEG (Poly(ethylene glycol) diacrylate, average Mn 700) as the polymerizable liquid and 5% of Diphenyl(2,4,6-trimethylbenzoyl)phosphine oxide as the photoinitiator. Processing conditions were otherwise the same as for the previously fabricated triacrylate parts.

EXAMPLE 17

Flexibility of Hydrogel Based Parts

The cylindrical cage structure produced in Example 23 above and shown in FIG. 25 was manually positioned between two glass microscope slides and pressure manually applied until the cylindrical cage structure was deformed and substantially flat. Manual pressure was then released, and the cage structure returned to its previous substantially cylindrical form. The flexibility, resiliency, and shape memory properties of the articles make them attractive for a variety of uses, including but not limited to stents for various biomedical applications.

EXAMPLE 18

Fabrication of Intraluminal Stents for Therapeutic Use

Stents are typically used as adjuncts to percutaneous transluminal balloon angioplasty procedures, in the treatment of occluded or partially occluded arteries and other blood vessels. As an example of a balloon angioplasty procedure, a guiding catheter or sheath is percutaneously introduced into the cardiovascular system of a patient through a femoral artery and advanced through the vasculature until the distal end of the guiding catheter is positioned at a point proximal to the lesion site. A guidewire and a dilatation catheter having a balloon on the distal end are introduced through the guiding catheter with the guidewire sliding within the dilatation catheter. The guidewire is first advanced out of the guiding catheter into the patient's vasculature and is directed across the vascular lesion. The dilatation catheter is subsequently advanced over the previously advanced guidewire until the dilatation balloon is properly positioned across the vascular lesion. Once in position across the lesion, the expandable balloon is inflated to a predetermined size with a radiopaque liquid at relatively high pressure to radially compress the atherosclerotic plaque of the lesion against the inside of the artery wall and thereby dilate the lumen of the artery. The balloon is then deflated to a small profile so that the dilatation catheter can be withdrawn from the patient's vasculature and blood flow resumed through the dilated artery.

Balloon angioplasty sometimes results in short or long term failure. That is, vessels may abruptly close shortly after the procedure or restenosis may occur gradually over a period of months thereafter. To counter restenosis following angioplasty, implantable intraluminal prostheses, commonly referred to as stents, are used to achieve long term vessel patency. A stent functions as scaffolding to structurally support the vessel wall and thereby maintain luminal patency, and are transported to a lesion site by means of a delivery catheter.

Types of stents may include balloon expandable stents, spring-like, self-expandable stents, and thermally expandable stents. Balloon expandable stents are delivered by a dilation catheter and are plastically deformed by an expandable member, such as an inflation balloon, from a small initial diameter to a larger expanded diameter. Self-expanding stents are formed as spring elements which are radially compressible about a delivery catheter. A compressed self-expanding stent is typically held in the compressed state by a delivery sheath. Upon delivery to a lesion site, the delivery sheath is retracted allowing the stent to expand. Thermally expandable stents are formed from shape memory alloys which have the ability to expand from a small initial diameter to a second larger diameter upon the application of heat to the alloy.

It may be desirable to provide localized pharmacological treatment of a vessel at the site being supported by a stent. Thus, sometimes it is desirable to utilize a stent both as a support for a lumen wall as well as a delivery vehicle for one or more pharmacological agents. Unfortunately, the bare metallic materials typically employed in conventional stents are not generally capable of carrying and releasing pharmacological agents. Previously devised solutions to this dilemma have been to join drug-carrying polymers to metallic stents. Additionally, methods have been disclosed wherein the metallic structure of a stent has been formed or treated so as to create a porous surface that enhances the ability to retain applied pharmacological agents. However, these methods have generally failed to provide a quick, easy and inexpensive way of loading drugs onto intraluminal prostheses, such as stents. In addition, only small amounts of drugs can be loaded into thin polymeric coatings.

Intraluminal prostheses, such as stents have been developed using various polymeric materials and/or coatings of polymeric materials to overcome the limitations of conventional metallic prostheses. However, it would be desirable to be able to adjust various mechanical properties (e.g., modulus, hoop strength, flexibility, etc.) of polymeric intraluminal prostheses. For example, for intraluminal prostheses used to deliver pharmacological agents, it would be desirable to be able to adjust the elution rate of a pharmacological agent therefrom. As another example, it would be desirable to be able to adjust the degradation rate and/or the nature of degradation of the polymeric material.

According to embodiments of the present example, methods of manufacturing polymeric intraluminal prostheses (e.g., formed from polymeric material to include suitably functionalized PEG, PLGA, polycaprolactone, gelatin, etc) include annealing the polymeric material to selectively modify the crystallinity or crystalline structure thereof is accomplished by the methods described herein, including but not limited to those set forth in connection with cylindrical cage structures as described above.

Pharmacological agents disposed on or within the polymeric material may include, but are not limited to, agents selected from the following categories: antineoplastics, antimitotics, antiinflammatories, antiplatelets, anticoagulants, antifibrins, antithrombins, antiproliferatives, antibiotics, antioxidants, immunosuppressives, antiallergic substances, and combinations thereof.

According to other embodiments of the present invention, the degree of molecular crosslinking of the polymeric material of an intraluminal prostheses may be modified by subjecting the polymeric material to chemical treatment and/or irradiation. The polymeric material may be subjected to chemical treatment and/or irradiation before, during and/or after annealing. Such treatments may also act as a sterilization step.

EXAMPLE 19

Fabrication of Therapeutic Microneedle Arrays

Many promising new therapeutics are large biomolecules, such as peptides, proteins, antibodies, and nucleic acids. These molecules can be too large, fragile, or insoluble for delivery by traditional routes of introduction. Hypodermic injection (including intravascular, intramuscular, etc.) enables the delivery of sensitive therapeutics, but they induce pain, provide opportunities for accidental needle sticks, and produce sharp, biohazardous waste. Furthermore, in the case of vaccine delivery, hypodermic needles do not deliver doses to the optimum location to elicit an immune response; they penetrate into muscle, a region known to have a lower density of immunologically sensitive cells than skin. Transdermal patches are effective for select time-released drugs (like nicotine and motion sickness medications), but the epidermis (specifically the stratum corneum) limits the diffusion of most drugs (>500 Da) through the skin. Clearly, the ability to transport therapeutics effectively into the body remains a significant challenge.

While there are limitations to traditional transdermal drug delivery, which typically relies on the passive diffusion of therapeutics through the skin, this route of administration remains very promising.

Using the apparatus described in the Examples above and photopolymerizable, biocompatible and biodegradable resins (suitably functionalized PEG, PLGA, polycaprolactone, gelatin, etc) are used in combination with therapeutics and vaccine elements (antigens, adjuvants, etc), to produce therapeutic microneedle arrays having essentially the same structure or appearance as those shown above. Those skilled in the art will appreciate numerous different structures and architectures for such therapeutic microneedle arrays which can be produced by the methods and apparatus described herein.

EXAMPLE 20

Dependence of Vertical Resolution on Fabrication Speed

During the part build process the controller image processing unit (IPU) in some embodiments is constantly updating images of cross sectional layers of the part. The maximum speed of image update f can in some embodiments vary from 1 frame per second up to 1000 frames per second, depending on the hardware.

If the desired vertical resolution is delta then during the build process the advancement dz of the part carrier during one image frame should be less than delta. If the fabrication speed is v then dz is given by $$dz = \frac{v}{f}$$

In order to achieve resolution delta, fabrication speed v should be less than the maximum fabrication speed $v_{max}$ given by $$v_{max} = \Delta f$$

Two chess piece parts similar to those illustrated above were made with a carrier advancement speed of 250 mm/hour and 500 mm/hour. The maximum frame rate of the particular IPU used to make the parts was approximately 1 frame per second. The estimated resolution of these parts was 50 micrometers at 250 mm/hour, and 100 micrometer at 500 mm/hour.

EXAMPLE 21

Increasing Fabrication Rate: Temperature

Increasing fabrication rate by pressure is described above. In addition, in the methods and apparatus set forth both generally and specifically above and below, fabrication rate can be increased by heating the polymerizable liquid, or resin, to reduce the viscosity thereof, to facilitate filling of the build zone with the polymerizable liquid or migration of the polymerizable liquid into the build zone (with or without increased pressure). Some resins, such as high performance resins including those noted above, may be solid at room temperature and pressure, and heating may be a convenient way to liquefy the same.

Figure 26:
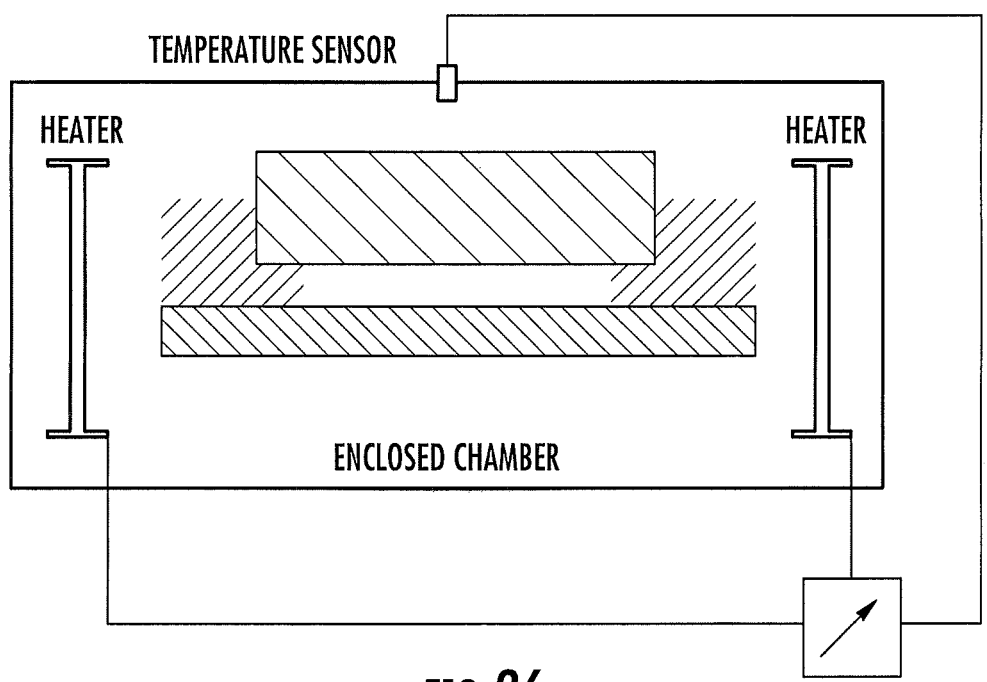
FIG. 26 schematically illustrates an embodiment of an apparatus of the present invention in which one or more heaters are included to reduce the viscosity of the polymerizable liquid.

Heating may be carried out by any suitable technique, such as with closed-oven infrared heaters operatively associated with a temperature sensor and controller, as schematically illustrated in FIG. 26. Numerous additional types and configurations of heaters may be used, alone or in combination with the foregoing and one another. Resistive heaters may be used, for example submersed in the polymerizable liquid on the build plate. Thermoelectric devices or Peltier heaters can be used, for example contacting the build plate and/or the polymerizable liquid. The polymerizable liquid can be preheated, in a storage reservoir and/or through various feed lines. One or more temperature sensors can be employed to detect ambient (in chamber) temperature, build plate temperature, carrier temperature, polymerizable liquid temperature (e.g., at any point, such as on the build plate), etc.

In some embodiments, the polymerizable liquid is heated by at least 5, 10, 20, 40, 60, 80, or 100 degrees Centigrade or more above room temperature.

In some embodiments, the polymerizable liquid has a viscosity of at least 100, 1,000, or 10,000 centipoise, up to 1,000,000 centipoise or more at 25 degrees Centigrade and atmospheric pressure (note 1 centipoise=1 milliPascal seconds). In some embodiments, such polymerizable liquids can have a viscosity when heated (e.g., by the amount described above) of not more than 1,000, 100, 10 or 1 centipoise. Specific end viscosity desired to be achieved will depend on factors such as the rate of fabrication desired, size and shape of the article being fabricated, the presence or absence of increased pressure, etc.

Viscosity can be measured by any suitable technique, for example by a Brookfield viscometer having a cone and plate geometry, with a cone angle of 1 degree, a 40 millimeter diameter, operated at 60 revolutions per minute.

Coolers can optionally be included if desired to more rapidly correct temperature (with heaters, or without heaters, e.g., to aid in dissipating heat generated exothermically by rapid photopolymerization. Again, any suitable cooler configuration can be used, generally operatively associated with a controller and temperature sensor as noted above. Heat exchangers, heat sinks, refrigerants, thermoelectric devices such as Peltier coolers (which may also serve as Peltier heaters), etc. may be employed.

EXAMPLE 22

Feeding Resin Through the Carrier and Internal Feed Channels

As discussed in Example 3 the speed of the object's formation depends on the linear dimension L of the object's bottom surface, viscosity of the resin atmospheric pressure P, and the height of the gap between the object and the bottom of the chamber h. The time τ which is required to fill the gap between the object and the bottom of the chamber is:

$$\tau \sim \left(\frac{L}{h}\right)^2 \frac{\eta}{P}$$

Figure 27:
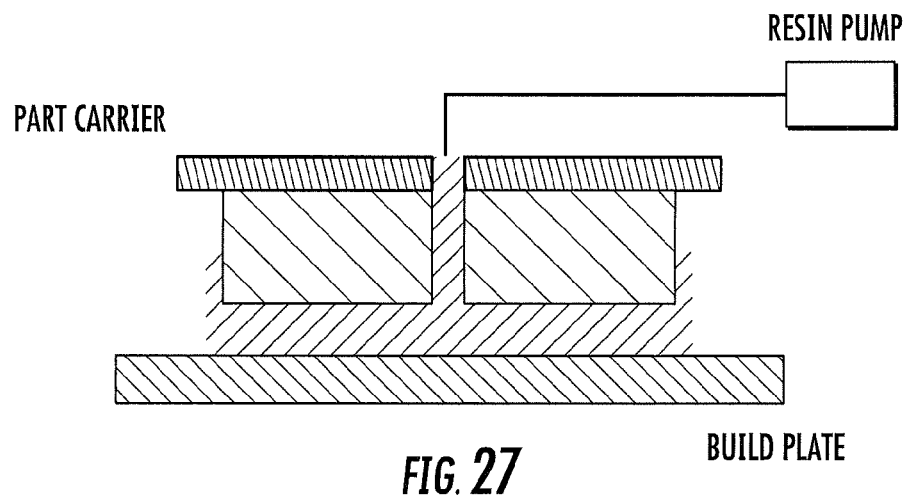
FIG. 27 schematically illustrates an embodiment of an apparatus of the present invention in which the build region is filled with polymerizable liquid fed through the carrier.

As one can see 10 fold increase in the part size results in 100 fold decrease in fabrication speed. To eliminate such strong dependence of fabrication speed on part size, polymerizable liquid (or resin) can be fed through the part carrier and through the part as shown in FIG. 27.

The pump can comprise any suitable pumping device, including but not limited to syringe pumps, gear pumps, peristaltic pumps, etc. The rate at which pump operates is controlled by a controller and depends on part geometry and speed of fabrication.

In this approach dependence of part fabrication rate on linear dimension L of the object's bottom surface, viscosity of the resin η, atmospheric pressure P, and the height of the gap between the object and the bottom of the chamber h is no longer limited by above equation but it is rather controlled by the rate at which resin pump operates, the rate of the curing reaction and the ability to mitigate heat removal from the curing reaction. The pump in this example could comprise a syringe pump, gear pump, or peristaltic pump. The pump operation could be included into feedback loop controlled by central processing unit where pumping rates depend on part geometry and desired fabrication speed.

EXAMPLE 23

Resin Feed Rate Control: Feed-Forward Control

During the part build process the resin consumption rate changes based on the cross sectional area of the part. A process to control resin delivery rate is described below. If the build speed is v and the cross section of the part A varies with time t as A(t) then resin delivery rate can be adjusted to correspond, in whole or in part, to:

$$R(t)=vA(t)$$

For example, during the build process a central processing unit (CPU) serving as a controller can in real time calculate the current cross section of the part, then calculate delivery rate based on a rule such as the equation above and communicate the calculated rate to a resin delivery pump controller (RDPC). The RDPC can then adjust the speed of the resin delivery pump based on the data received from CPU.

Such a feed-forward control system can be used alone or in combination with other feed forward and feed-back control systems (e.g., temperature and/or pressure control) as described above.

EXAMPLE 24

Feeding Polymerizable Liquid through External Feed Conduits

In some embodiments where polymerizable liquid is supplied through one or more channels formed in the carrier, it may be desired that some, or all, of the article being fabricated be solid throughout. In such cases, separate or external feed conduits in fluid communication with a (or each) channel supplying polymerizable liquid may be concurrently fabricated adjacent the article being fabricated (In contrast to one or more internal feed channels formed within the article being produced.

The polymerizable liquid can then be provided through the external feed conduit(s) to the build plate and fabrication zone. In some embodiments multiple such feed conduits may be constructed, e.g., 2, 10, 100, or 1000 or more, depending on the size of the article being fabricated. Such external feed conduits may be used in combination, concurrently or sequentially (e.g., alternatively), with internal feed channels (i.e., channels formed within the article being fabricated).

EXAMPLE 25

Fabrication With Multiple Distinct Resins with Multiple Feed Conduits

Articles can be fabricated using multiple resins by feeding the different resins through the build platform, and using them to create tubes or channels to deliver the resin to the correct area of the part being fabricated.

Figure 28:
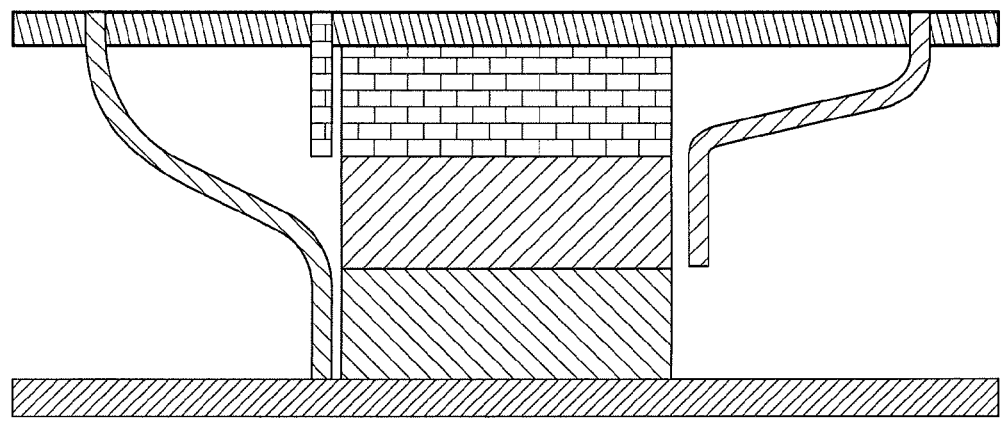
FIG. 28 schematically illustrates an embodiment of the invention in which external conduits are formed to facilitate feeding one or multiple polymerizable liquids from the carrier to the build region.

FIG. 28 illustrates the method that can be used to feed resin through the build platform, use it to fabricate the resin delivery channels in the necessary shape, and when necessary, feed extra resin to fabricate the part itself. When the section has finished fabrication, the channel is cured shut and another channel can begin feeding the next resin to continue fabricating the part.

EXAMPLE 26

Control of Method and Apparatus

Figure 29:
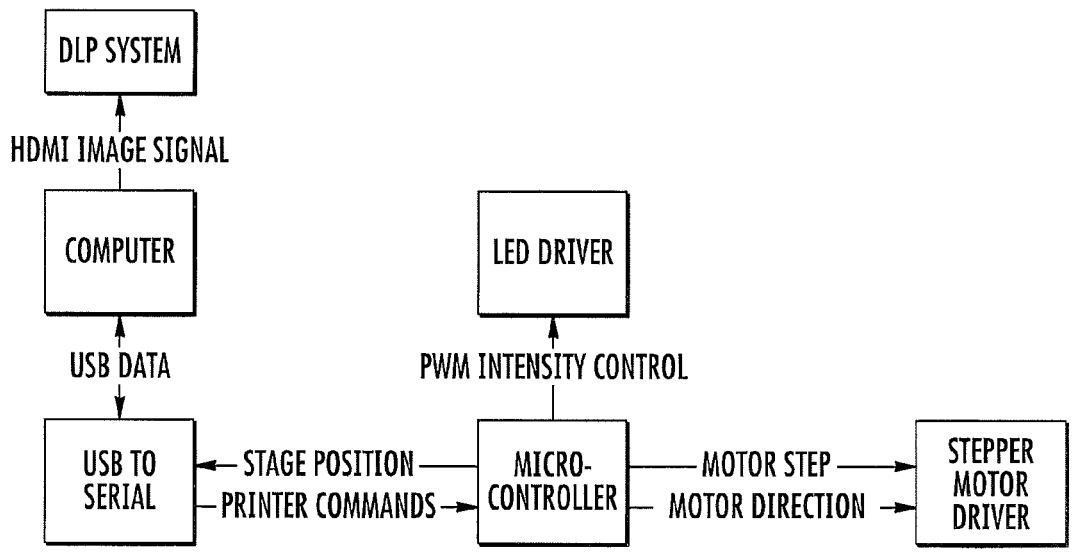
FIG. 29 is a first flow chart illustrating control systems and methods for carrying out the present invention.
Figure 30:
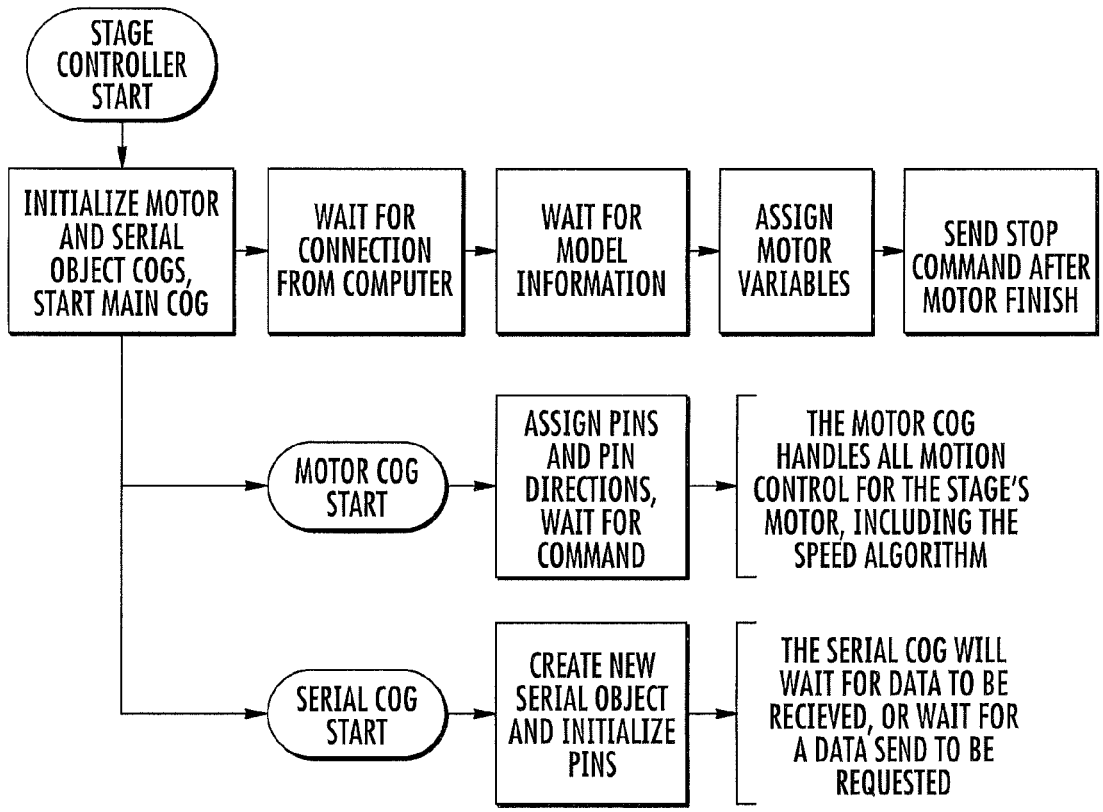
FIG. 30 is a second flow chart illustrating control systems and methods for carrying out the present invention.
Figure 31:
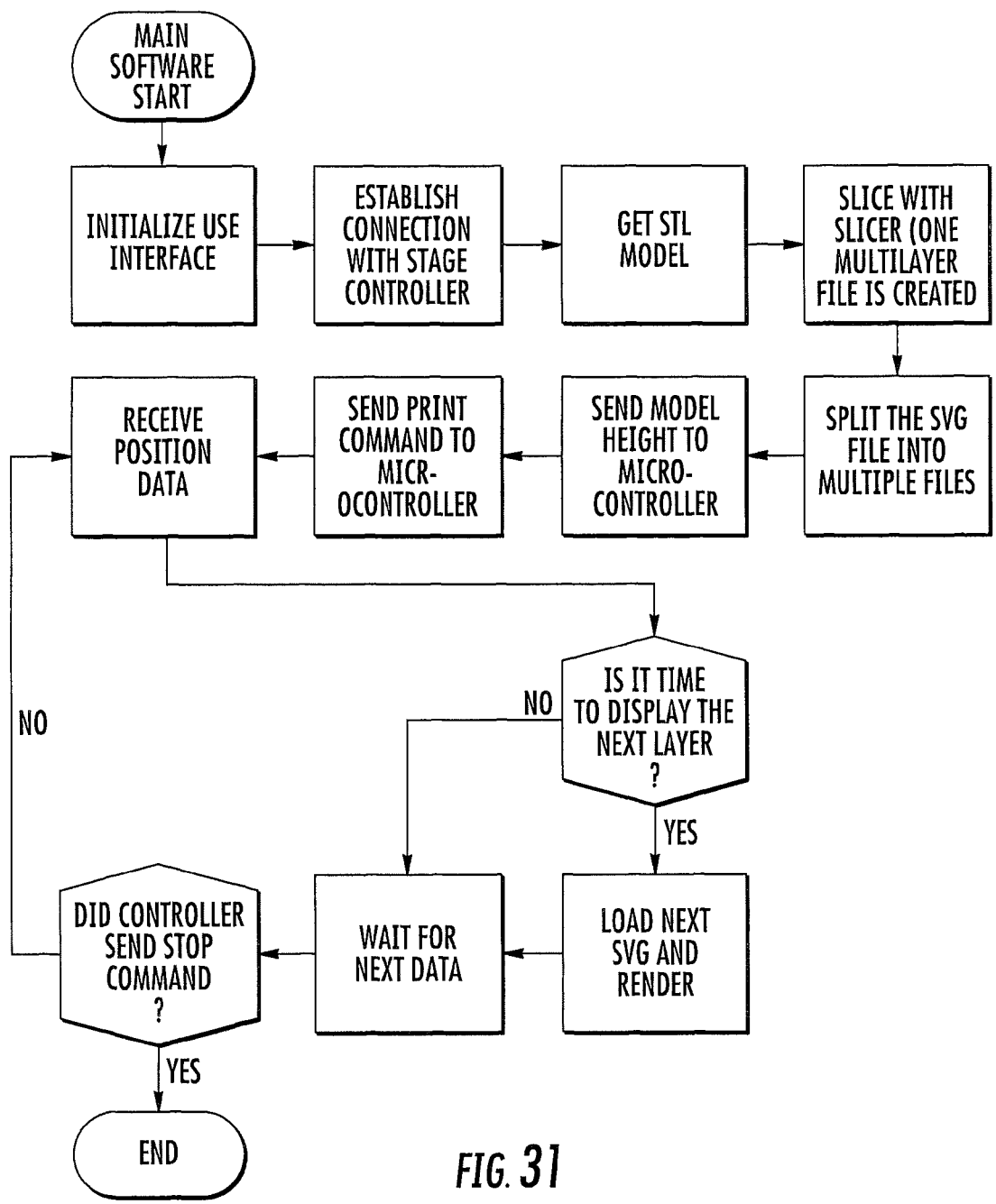
FIG. 31 is a third flow chart illustrating control systems and methods for carrying out the present invention.

A method and apparatus as described above may be controlled by a software program running in a general purpose computer with suitable interface hardware between that computer and the apparatus described above. Numerous alternatives are commercially available. Non-limiting examples of one combination of components is shown in FIGS. 29-31, where "Microcontroller" is Parallax Propeller, the Stepper Motor Driver is Sparkfun EasyDriver, the LED Driver is a Luxeon Single LED Driver, the USB to Serial is a Parallax USB to Serial converter, and the DLP System is a Texas Instruments LightCrafter system.

The foregoing is illustrative of the present invention, and is not to be construed as limiting thereof. The invention is defined by the following claims, with equivalents of the claims to be included therein.

That which is claimed is:

1. A method of forming a three-dimensional object, comprising:
    providing a carrier and an optically transparent member having a build surface, said carrier and said build surface defining a build region therebetween;
    filling said build region with a polymerizable liquid;
    irradiating said build region through said optically transparent member to form a solid polymer from said polymerizable liquid while concurrently advancing said carrier away from said build surface to form said three-dimensional object from said solid polymer, while also concurrently:
    (i) continuously maintaining a dead zone of polymerizable liquid in contact with said build surface, and
    (ii) continuously maintaining a gradient of polymerization zone between said dead zone and said solid polymer and in contact with each thereof, said gradient of polymerization zone comprising said polymerizable liquid in partially cured form.

2. The method of claim 1, wherein said optically transparent member comprises a semipermeable member, and said continuously maintaining a dead zone is carried out by feeding an inhibitor of polymerization through said optically transparent member, thereby creating a gradient of inhibitor in said dead zone and optionally in at least a portion of said gradient of polymerization zone.

3. A method of forming a three-dimensional object, comprising:
    providing a carrier and an optically transparent member having a build surface, said carrier and said build surface defining a build region therebetween;
    filling said build region with a polymerizable liquid;
    irradiating said build region through said optically transparent member to form a solid polymer from said polymerizable liquid while concurrently advancing said carrier away from said build surface to form said three-dimensional object from said solid polymer, while also concurrently:
    (i) continuously maintaining a dead zone of polymerizable liquid in contact with said build surface, and
    (ii) continuously maintaining a gradient of polymerization zone between said dead zone and said solid polymer and in contact with each thereof, said gradient of polymerization zone comprising said polymerizable liquid in partially cured form;
    wherein said optically transparent member is comprised of a semipermeable fluoropolymer, a rigid gas-permeable polymer, porous glass, or a combination thereof.

4. The method of claim 1, wherein said irradiating step is carried out by maskless photolithography.

5. The method claim 1, wherein said gradient of polymerization zone and said dead zone together have a thickness of from 1 to 1000 microns.

6. The method of claim 1, wherein said gradient of polymerization zone is maintained for a time of at least 5 seconds.

7. The method of claim 1, further comprising the step of disrupting said gradient of polymerization zone for a time sufficient to form a cleavage line in said three-dimensional object.

8. The method of claim 1, further comprising the step of heating said polymerizable liquid to reduce a viscosity thereof in said build region.

9. The method of claim 1, wherein said carrier has at least one channel formed therein, and said filling step is carried out by passing or forcing said polymerizable liquid into said build region through said at least one channel.

10. The method of claim 1, wherein said irradiating step is carried out with actinic radiation.

11. The method of claim 1, wherein said concurrently advancing is carried out at a cumulative rate of at least 10 microns per second.

12. The method of claim 1, wherein:
    a total surface area of the build region occupies at least seventy percent of a total surface area of the build surface; and/or
    wherein lateral movement of the carrier and object in any direction is not more than thirty percent of a width of said build region in the corresponding direction.

13. The method of claim 2, wherein (a) said polymerizable liquid comprises a free radical polymerizable liquid and said inhibitor comprises oxygen, or (b) said polymerizable liquid comprises an acid-catalyzed or cationically polymerizable liquid, and said inhibitor comprises a base.

14. A method of forming a three-dimensional object, comprising:
    providing a carrier and an optically transparent member having a build surface, said carrier and said build surface defining a build region therebetween;
    filling said build region with a polymerizable liquid;
    irradiating said build region with actinic radiation through said optically transparent member to form a solid polymer from said polymerizable liquid while concurrently advancing said carrier away from said build surface to form said three-dimensional object from said solid polymer, while also concurrently:
    (i) continuously maintaining a dead zone of polymerizable liquid in contact with said build surface, and
    (ii) continuously maintaining a gradient of polymerization zone between said dead zone and said solid polymer and in contact with each thereof, said gradient of polymerization zone comprising said polymerizable liquid in partially cured form;
    wherein said gradient of polymerization zone and said dead zone together have a thickness of from 1 to 1000 microns;
    wherein said gradient of polymerization zone is maintained for a time of at least 5 seconds.

15. The method of claim 14, wherein:
    said optically transparent member comprises a semipermeable member, and said continuously maintaining a dead zone is carried out by feeding an inhibitor of polymerization through said optically transparent member, thereby creating a gradient of inhibitor in said dead zone and optionally in at least a portion of said gradient of polymerization zone; and said semipermeable member is comprised of a semipermeable fluoropolymer, a rigid gas-permeable polymer, porous glass, or a combination thereof.

16. The method of claim 15, wherein said optically transparent member is stationary.

17. The method of claim 16, wherein said semipermeable member comprises a flexible polymer film, there further being provided a tensioning member connected to said polymer film to fix and rigidify the film.

18. The method of claim 17, wherein said flexible polymer film comprises a fluoropolymer film.

19. A method of forming a three-dimensional object, comprising:

providing a carrier and an optically transparent member having a build surface, said carrier and said build surface defining a build region therebetween;

filling said build region with a polymerizable liquid;

irradiating said build region through said optically transparent member to form a solid polymer from said polymerizable liquid while concurrently advancing said carrier away from said build surface to form said three-dimensional object from said solid polymer, while also concurrently:

(i) continuously maintaining a dead zone of polymerizable liquid in contact with said build surface, and (ii) continuously maintaining a gradient of polymerization zone between said dead zone and said solid polymer and in contact with each thereof, said gradient of polymerization zone comprising said polymerizable liquid in partially cured form;

further comprising the steps of:

monitoring or detecting at least one process parameter and/or providing at least one known or predetermined process parameter; and then altering at least one process condition in response to said monitored process parameter or known or predetermined process parameter.

20. The method of claim 19, wherein:

said process parameter is expected consumption of polymerizable liquid; and said process condition is a rate of supply of polymerizable liquid.

21. The method of claim 15, and wherein (i) said polymerizable liquid comprises a free radical polymerizable liquid and said inhibitor comprises oxygen, or (ii) said polymerizable liquid comprises an acid-catalyzed or cationically polymerizable liquid, and said inhibitor comprises a base.

22. The method of claim 2, wherein said semipermeable member comprises a fluoropolymer film.

23. The method of claim 3, wherein said optically transparent member comprises a semipermeable member, and said continuously maintaining a dead zone is carried out by feeding an inhibitor of polymerization through said optically transparent member, thereby creating a gradient of inhibitor in said dead zone and optionally in at least a portion of said gradient of polymerization zone.

24. The method of claim 15, wherein said semipermeable member comprises a fluoropolymer film.

25. The method of claim 19, wherein said optically transparent member comprises a semipermeable member, and said continuously maintaining a dead zone is carried out by feeding an inhibitor of polymerization through said optically transparent member, thereby creating a gradient of inhibitor in said dead zone and optionally in at least a portion of said gradient of polymerization zone.

26. The method of claim 25, wherein said semipermeable member comprises a fluoropolymer film.

* * * * *